(12) United States Patent
Bertollo et al.

(10) Patent No.: US 11,298,124 B2
(45) Date of Patent: Apr. 12, 2022

(54) TISSUE ANCHOR

(71) Applicant: University College Dublin, National University of Ireland, Dublin (IE)

(72) Inventors: Nicky Bertollo, Dublin (IE); Seamus Morris, County Dublin (IE); Eoin O'Cearbhaill, County Dublin (IE)

(73) Assignee: Univ. College Dublin, National Univ. of Ireland, Dublin (IE)

( * ) Notice: Subject to any disclaimer, the term of this patent is extended or adjusted under 35 U.S.C. 154(b) by 170 days.

(21) Appl. No.: 16/341,199

(22) PCT Filed: Oct. 16, 2017

(86) PCT No.: PCT/EP2017/076305
§ 371 (c)(1),
(2) Date: Apr. 11, 2019

(87) PCT Pub. No.: WO2018/069543
PCT Pub. Date: Apr. 19, 2018

(65) Prior Publication Data
US 2019/0314012 A1    Oct. 17, 2019

(30) Foreign Application Priority Data
Oct. 14, 2016   (GB) .................................... 1617509

(51) Int. Cl.
*A61B 17/04* (2006.01)
*A61B 17/00* (2006.01)
(Continued)

(52) U.S. Cl.
CPC .......... *A61B 17/064* (2013.01); *A61B 5/6839* (2013.01); *A61B 17/0466* (2013.01);
(Continued)

(58) Field of Classification Search
CPC .............. A61B 17/064; A61B 17/0466; A61B 17/0643; A61B 2017/0496;
(Continued)

(56) References Cited

U.S. PATENT DOCUMENTS

| 8,894,683 B2 | 11/2014 | Weadock |
| 2001/0051815 A1 | 12/2001 | Esplin |

(Continued)

FOREIGN PATENT DOCUMENTS

| DE | 102010022434 A1 | 12/2011 |
| WO | 2012150553 A1 | 11/2012 |

OTHER PUBLICATIONS

Nov. 24, 2017 International Search Report and Written Opinion in International Application No. PCT/EP2017/076305.

*Primary Examiner* — Darwin P Erezo
*Assistant Examiner* — Raihan R Khandker
(74) *Attorney, Agent, or Firm* — Vitale, Vickrey, Niro & Gasey LLP

(57) ABSTRACT

The present invention provides a tissue anchor and a system and method employing same, the anchors including a body having a first section and a second section reversibly engagable with one another, each section including a plurality of barbs in the form of microneedles projecting from the underside therefore, the barbs on one section being inclined towards barbs on the other section, such that tissue may be captured and deformed between the barbs through displacement of the first section relative to the second section in order to achieve robust retention of the tissue anchor at a deployment site.

20 Claims, 35 Drawing Sheets

(51) Int. Cl.
*A61B 17/08* (2006.01)
*A61B 17/064* (2006.01)
*A61B 5/00* (2006.01)
*A61M 37/00* (2006.01)
*A61B 5/145* (2006.01)
*A61N 1/04* (2006.01)
*A61B 5/318* (2021.01)
*A61B 5/389* (2021.01)

(52) U.S. Cl.
CPC ..... *A61M 37/0015* (2013.01); *A61B 5/14532* (2013.01); *A61B 5/318* (2021.01); *A61B 5/389* (2021.01); *A61B 2017/00004* (2013.01); *A61B 2017/0641* (2013.01); *A61B 2017/0645* (2013.01); *A61B 2017/081* (2013.01); *A61M 2037/0023* (2013.01); *A61M 2037/0046* (2013.01); *A61N 1/0456* (2013.01)

(58) Field of Classification Search
CPC .............. A61B 2017/086; A61B 17/08; A61B 17/0401; A61B 2017/0412; A61B 2017/0427; A61B 2017/0641; A61B 17/11; A61B 2017/081; A61B 2017/0466
See application file for complete search history.

(56) References Cited

U.S. PATENT DOCUMENTS

| | | | |
|---|---|---|---|
| 2004/0260340 A1* | 12/2004 | Jacobs | A61B 17/08 606/213 |
| 2005/0209542 A1 | 9/2005 | Jacobs | |
| 2005/0251155 A1 | 11/2005 | Orban | |
| 2007/0021779 A1 | 1/2007 | Garvin | |
| 2013/0282056 A1* | 10/2013 | Fleischmann | A61B 17/08 606/218 |
| 2015/0335871 A1* | 11/2015 | Lim | A61M 37/0015 83/13 |

* cited by examiner

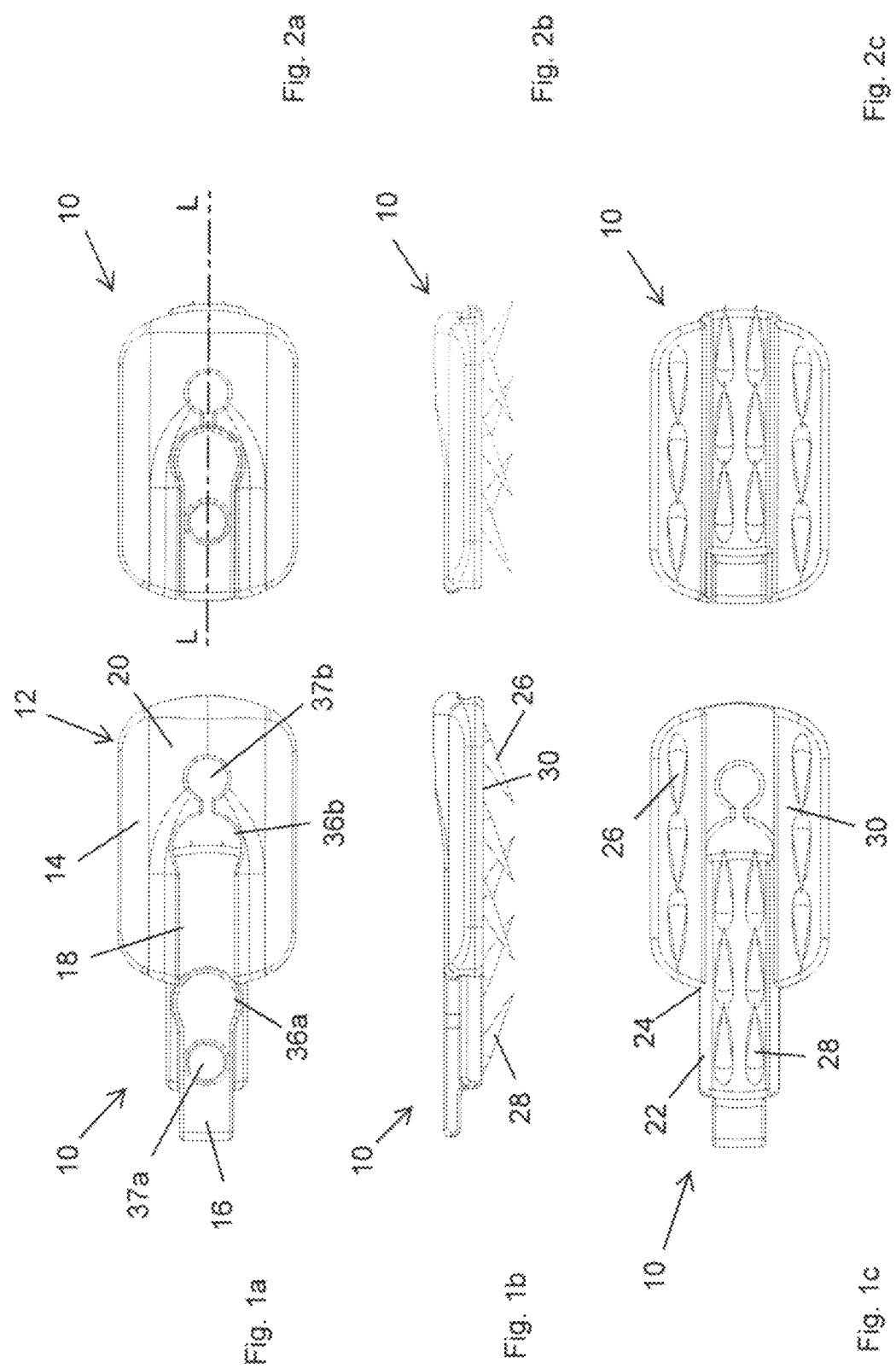

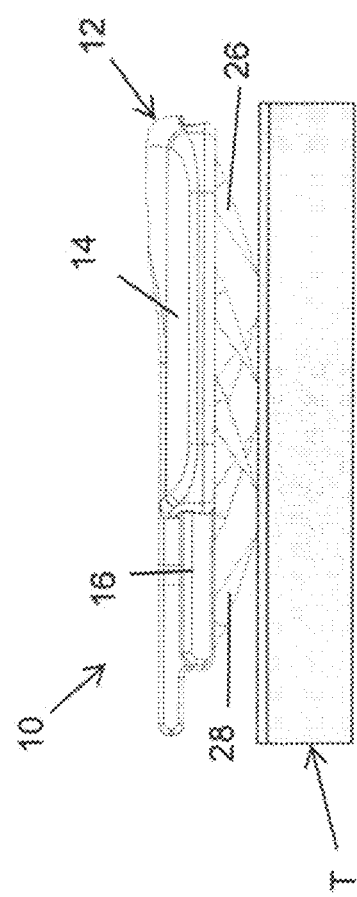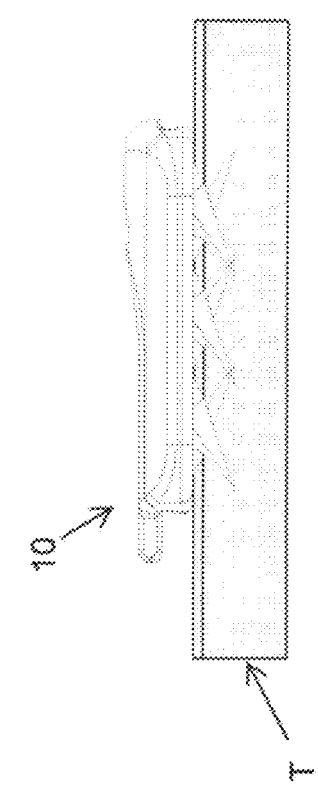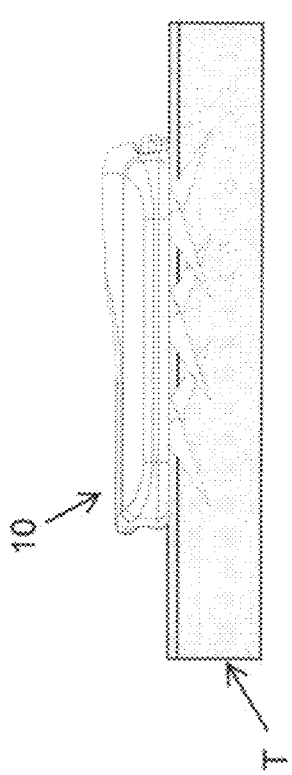

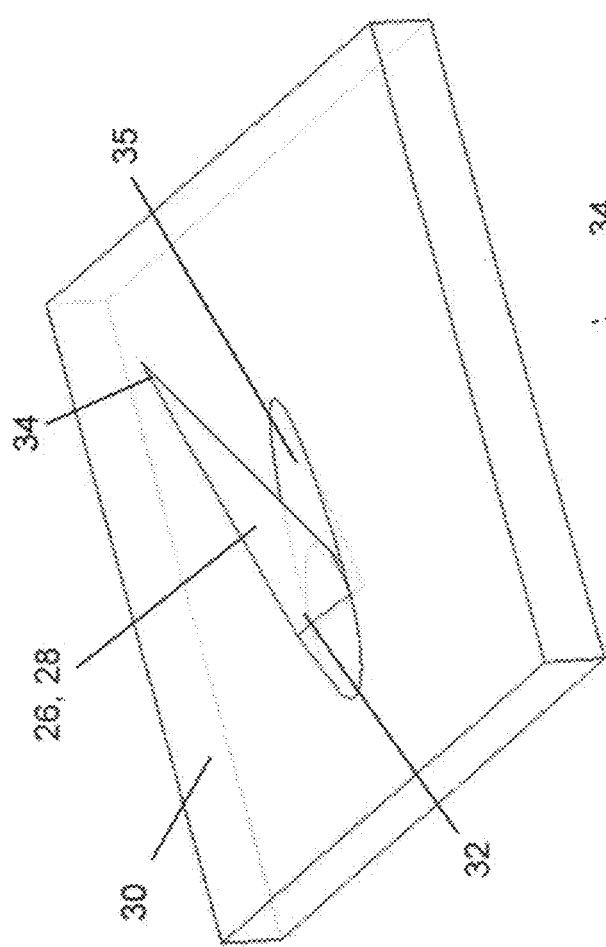
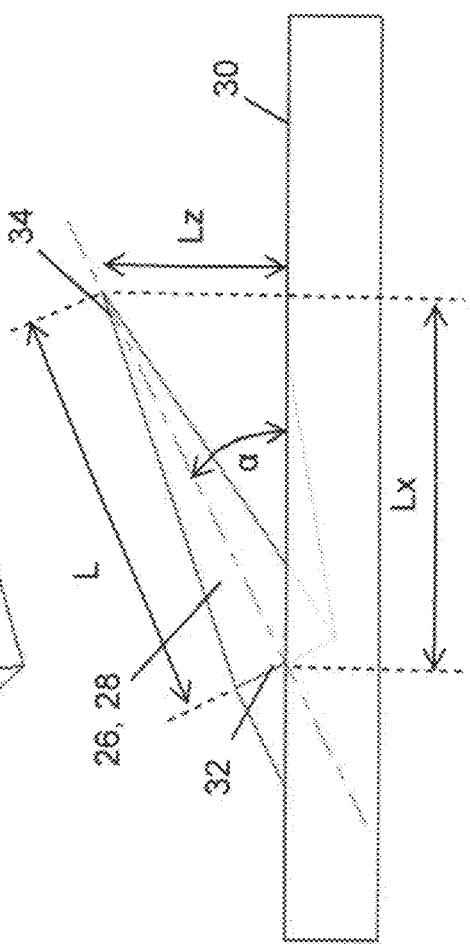

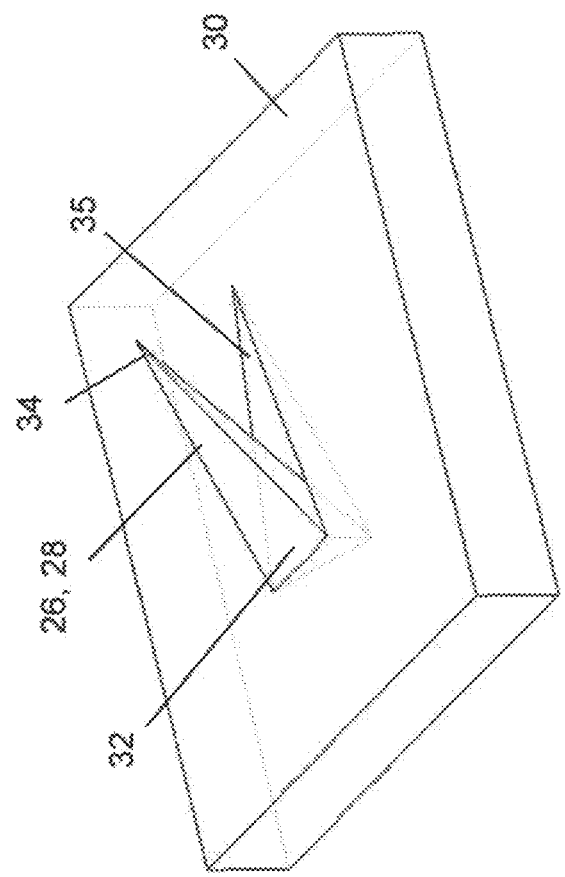

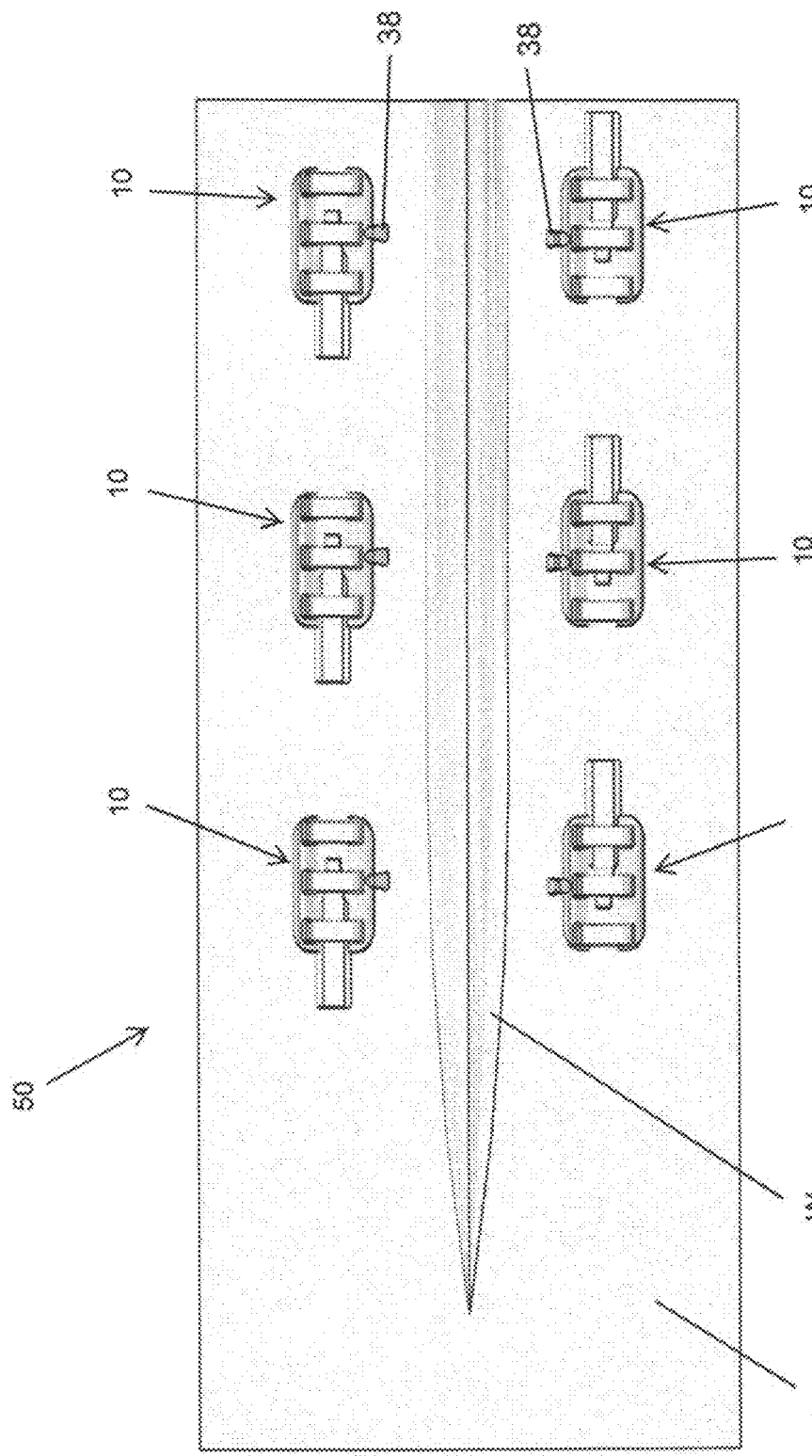

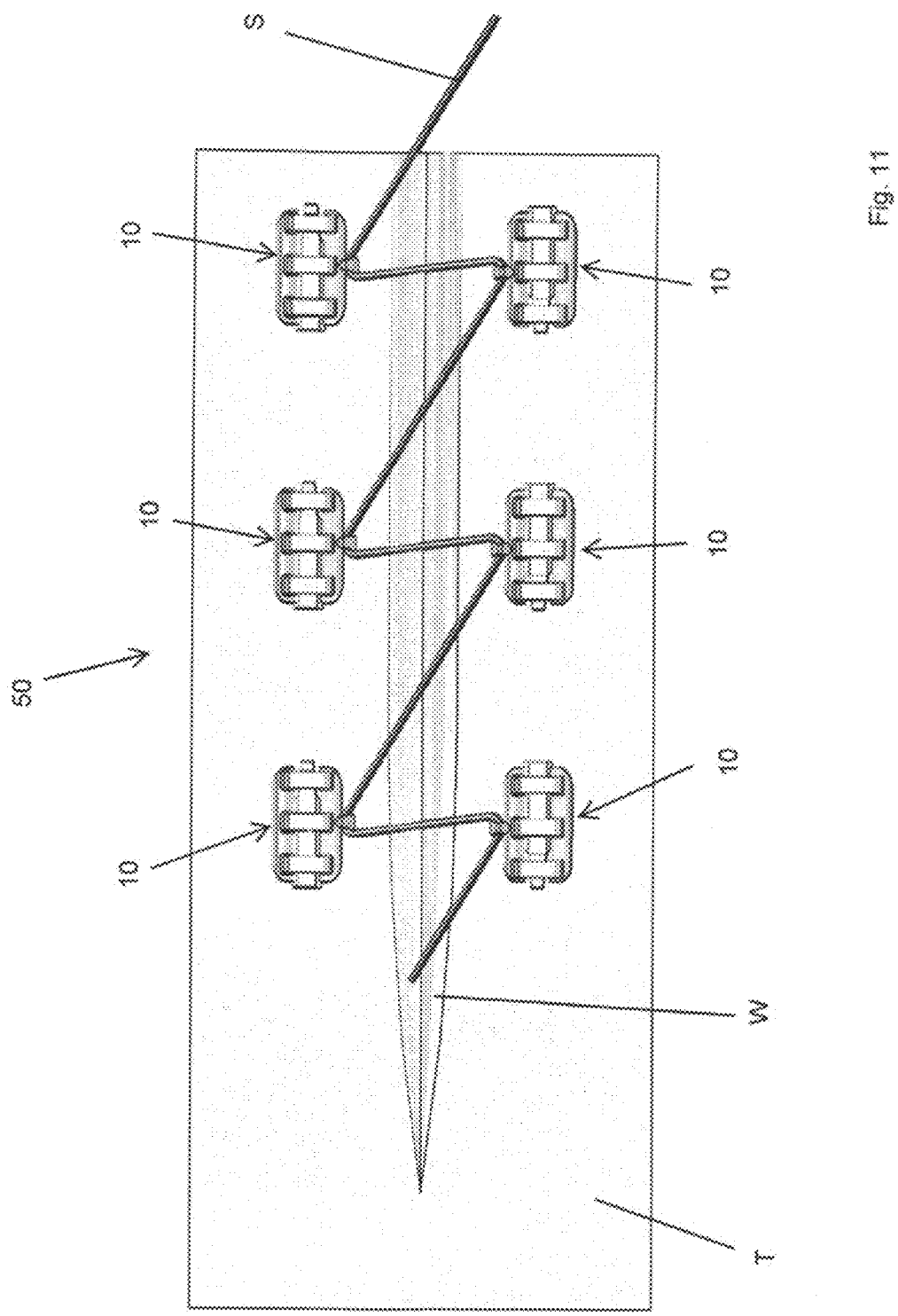

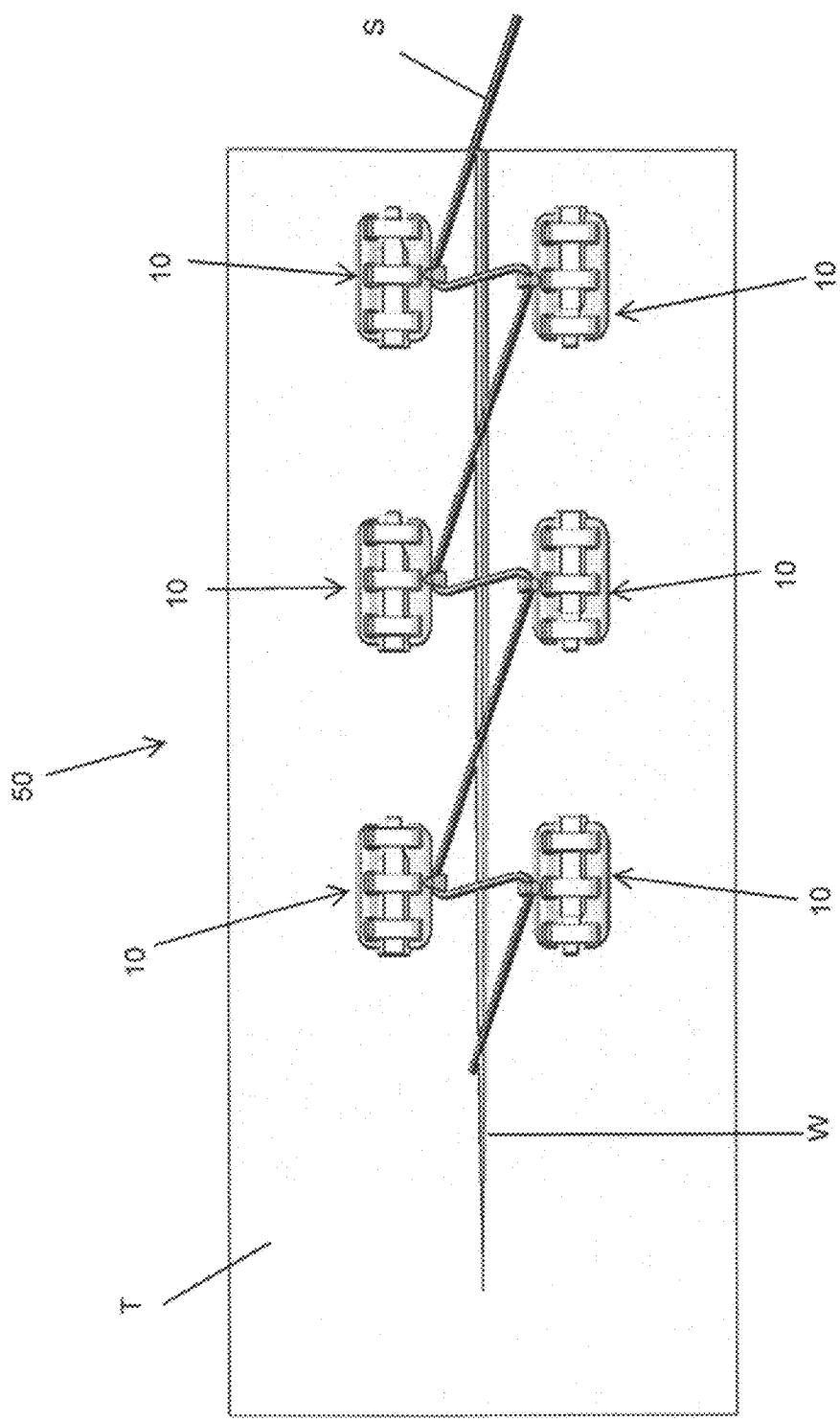

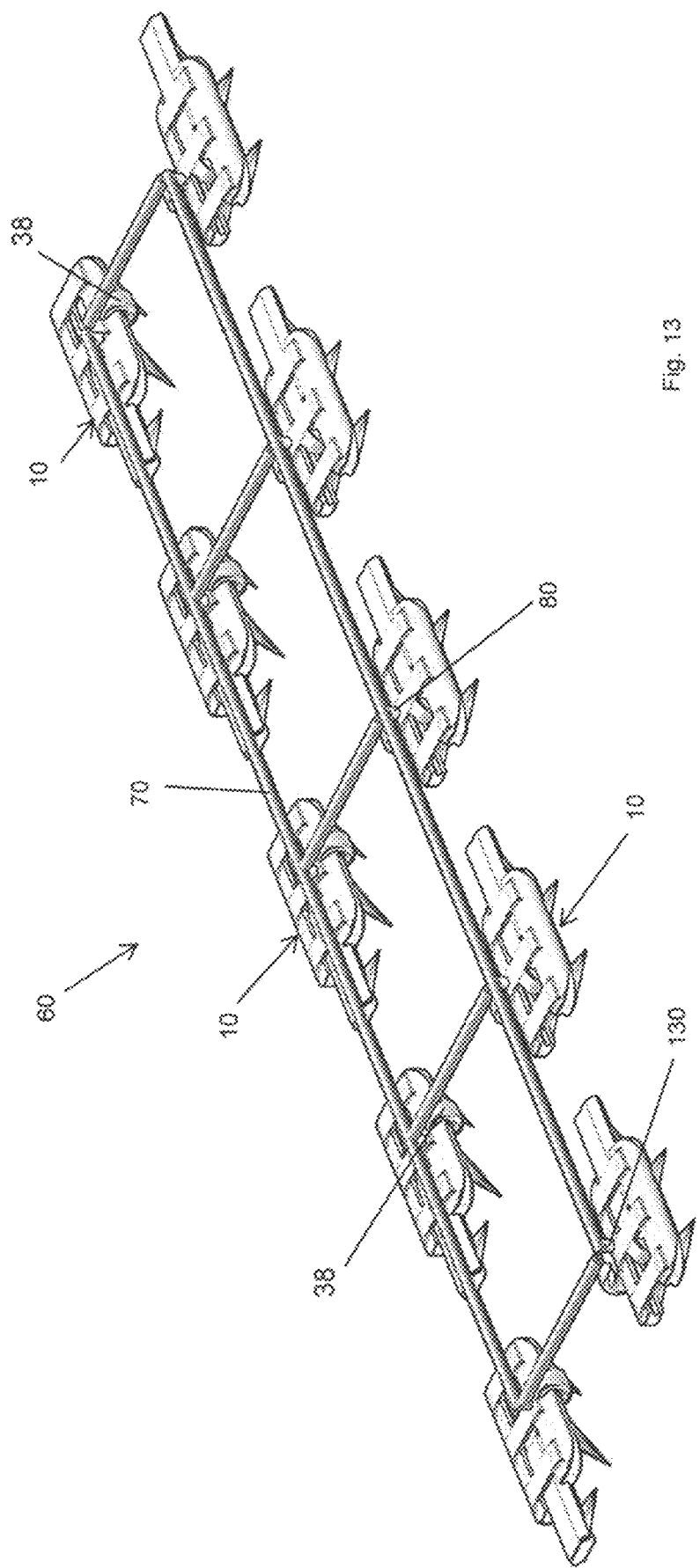

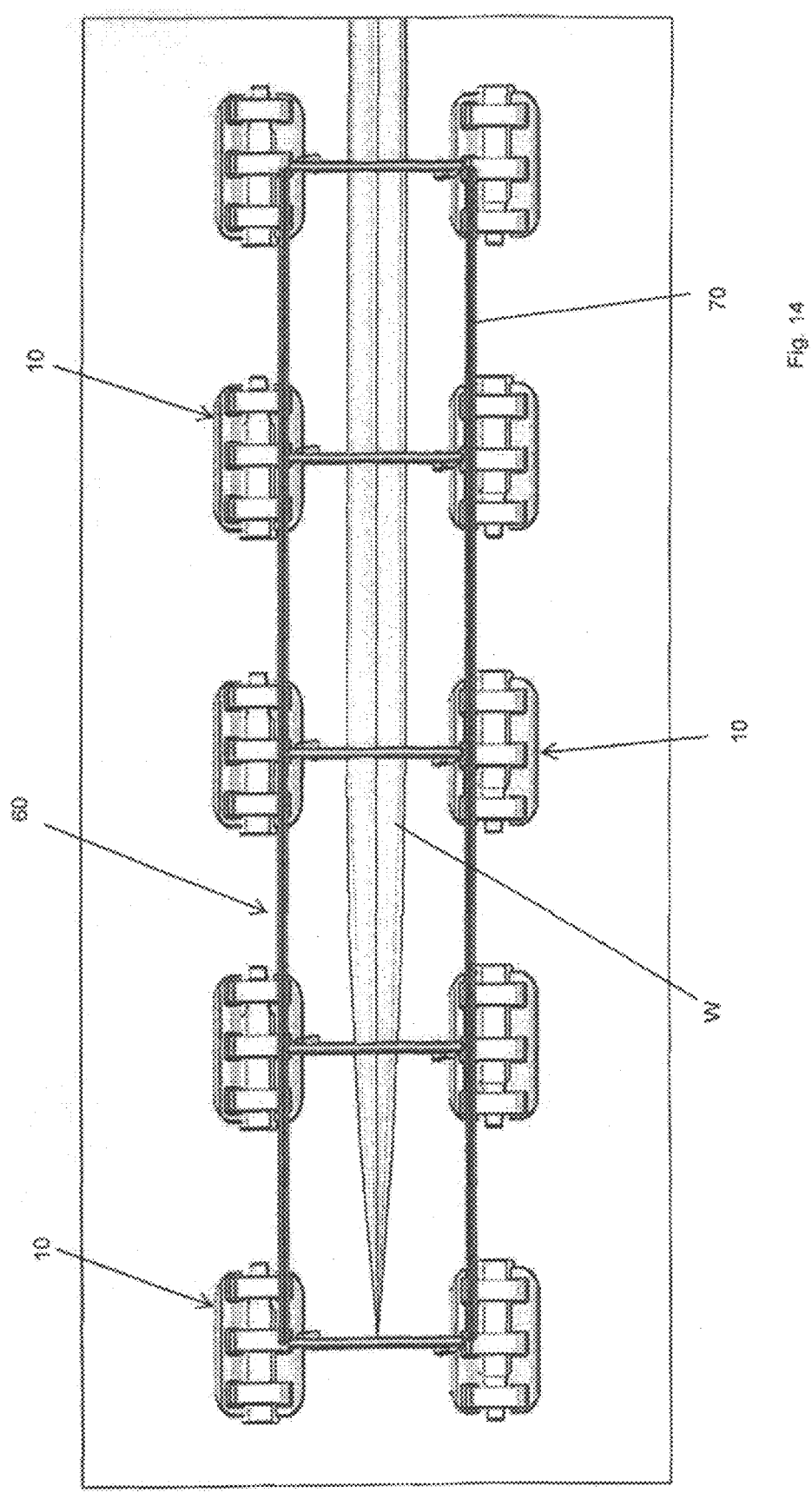

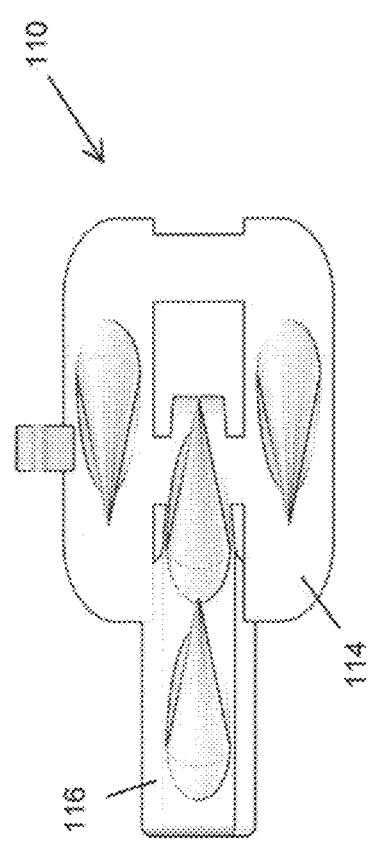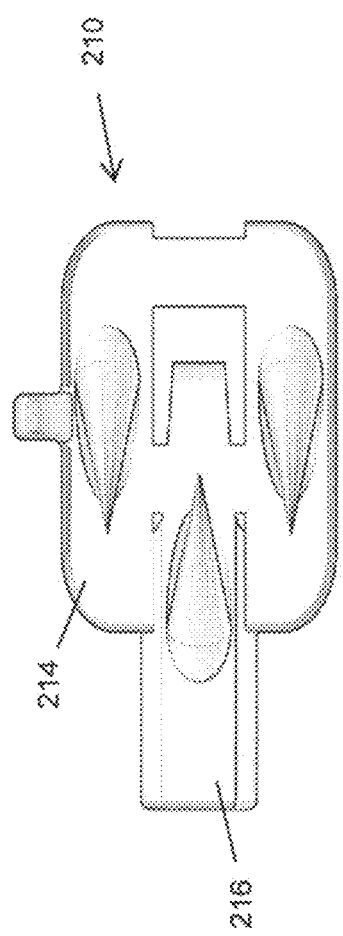

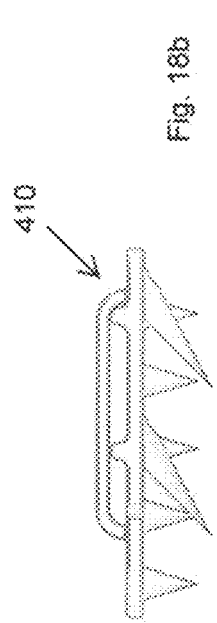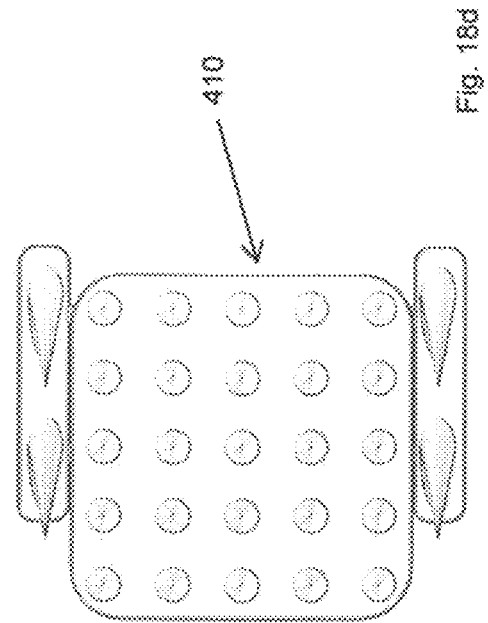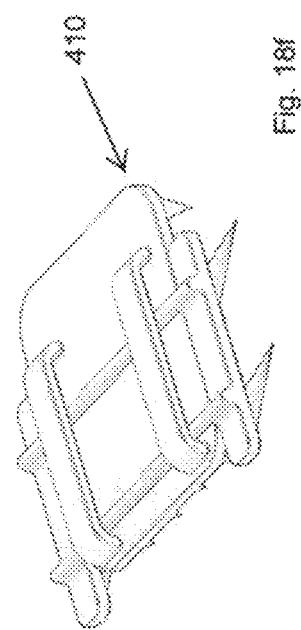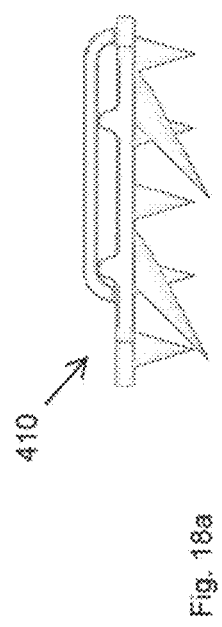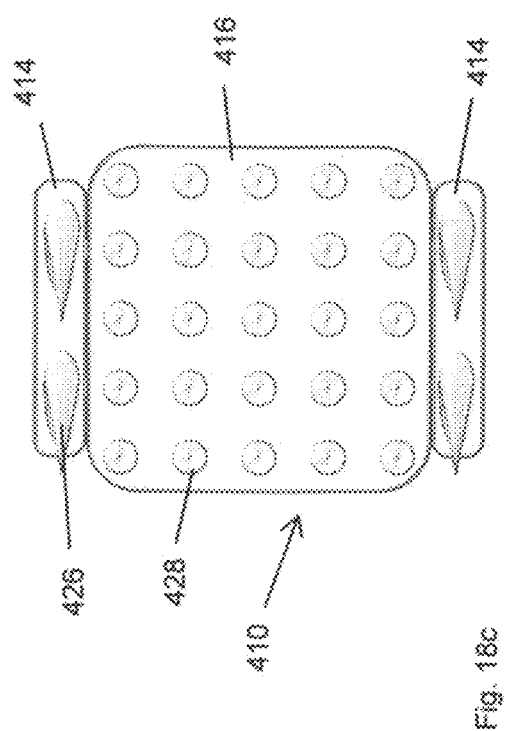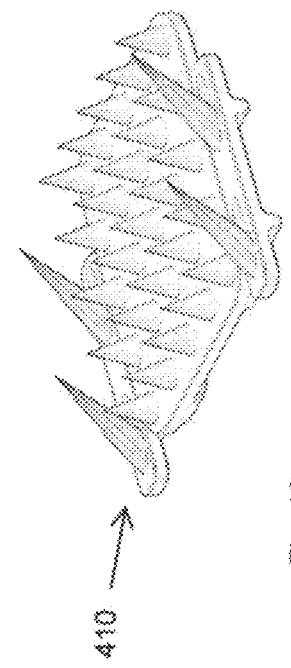

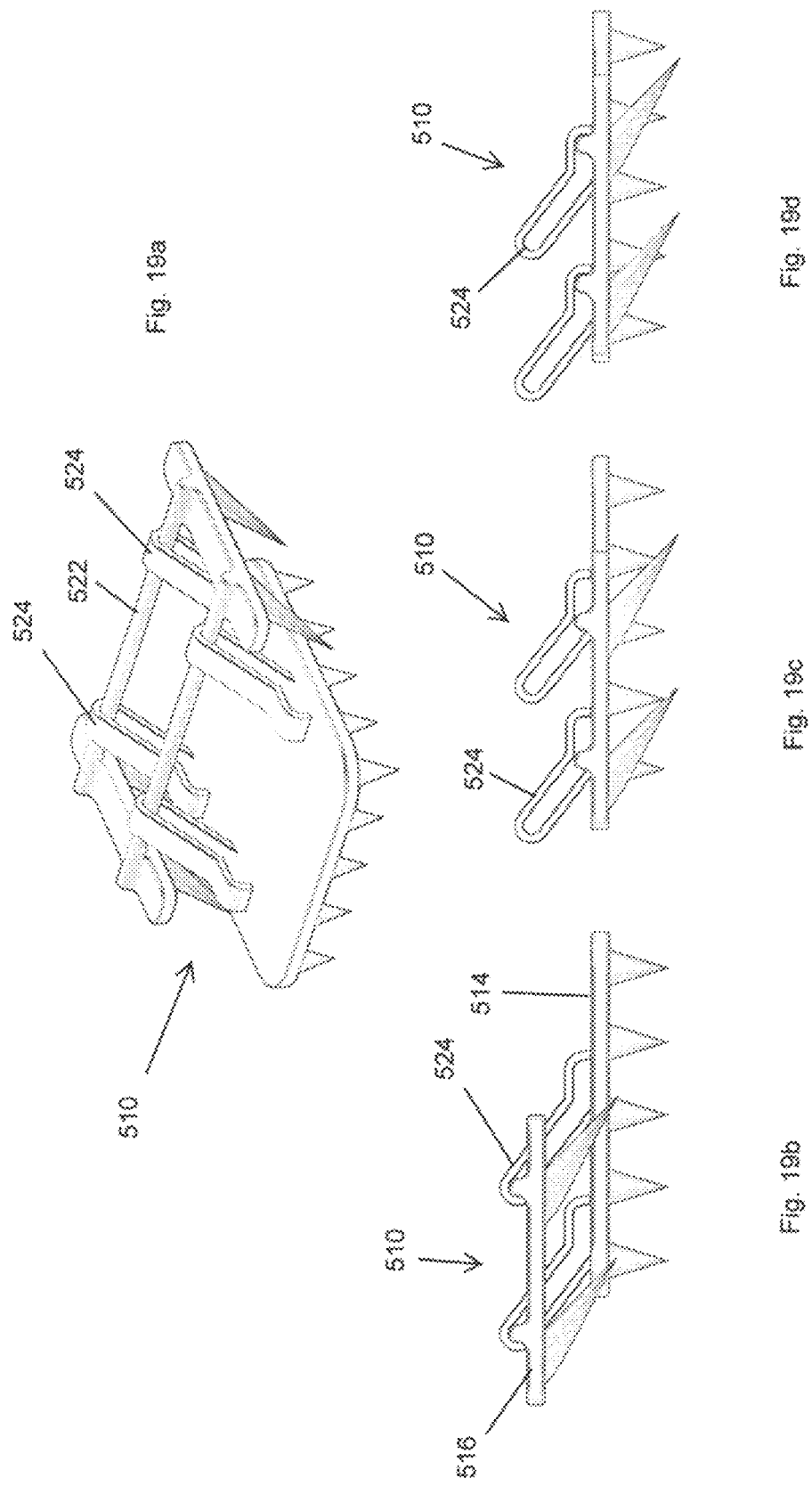

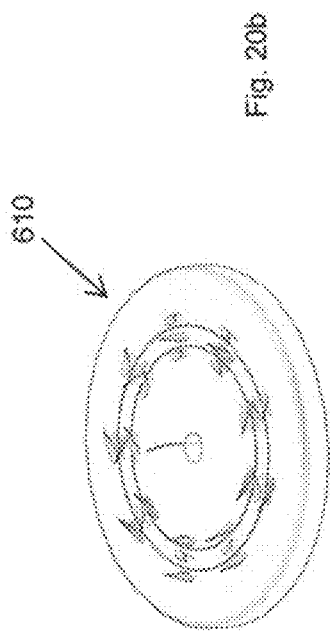
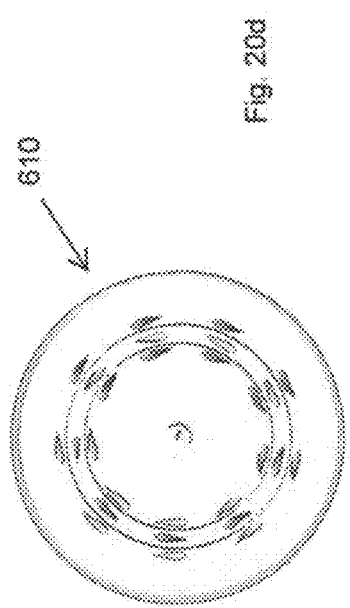
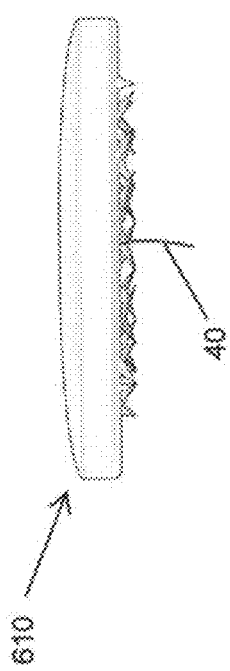
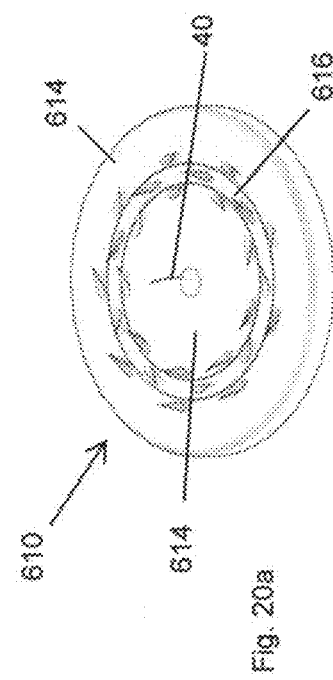
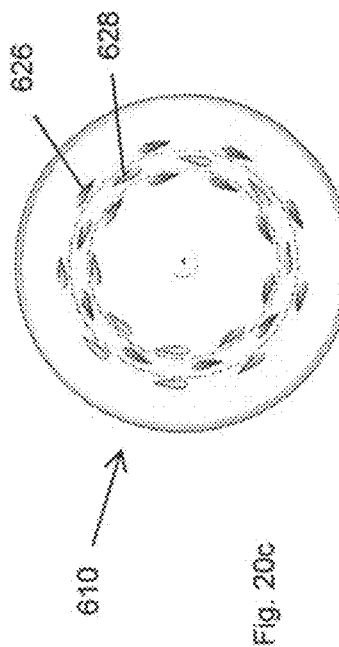

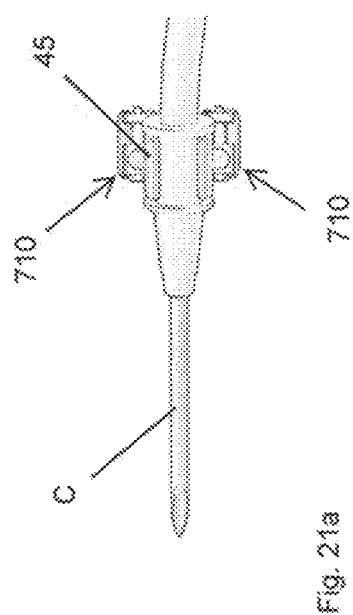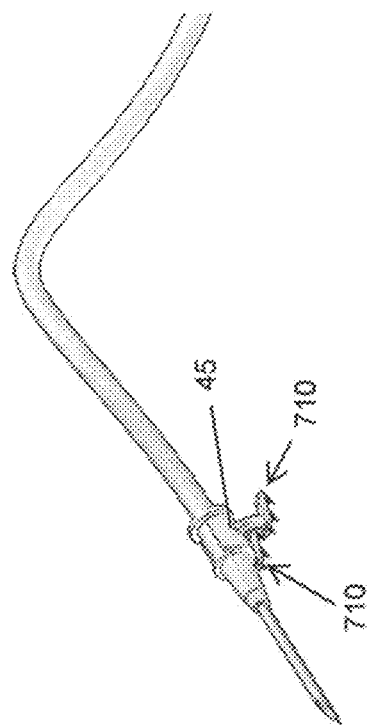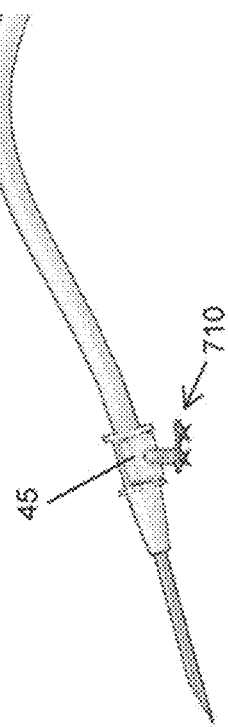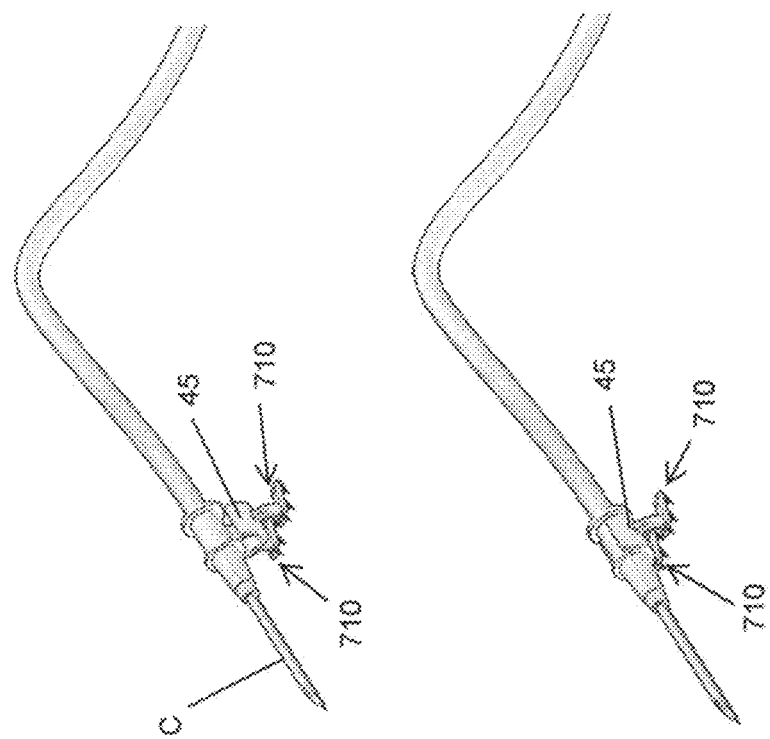

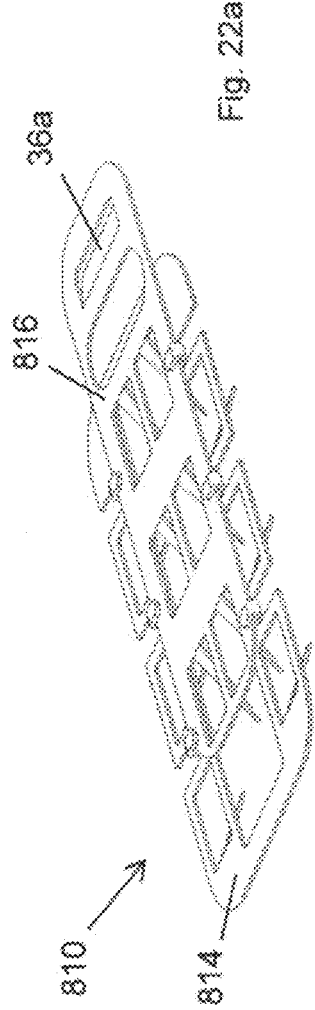
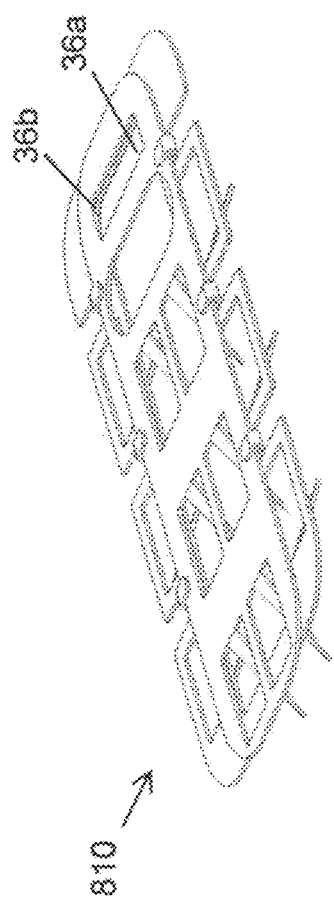
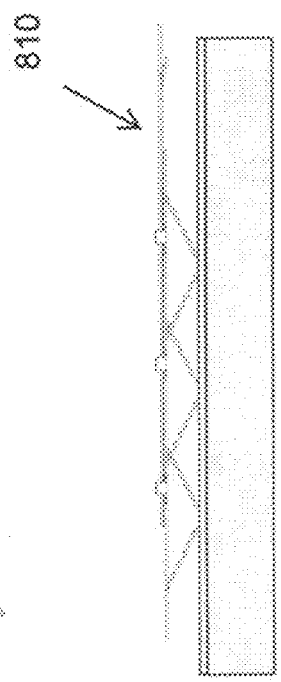
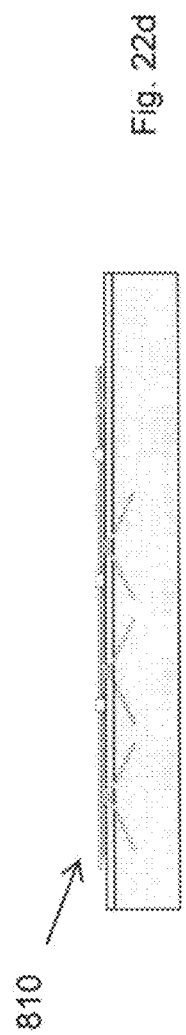

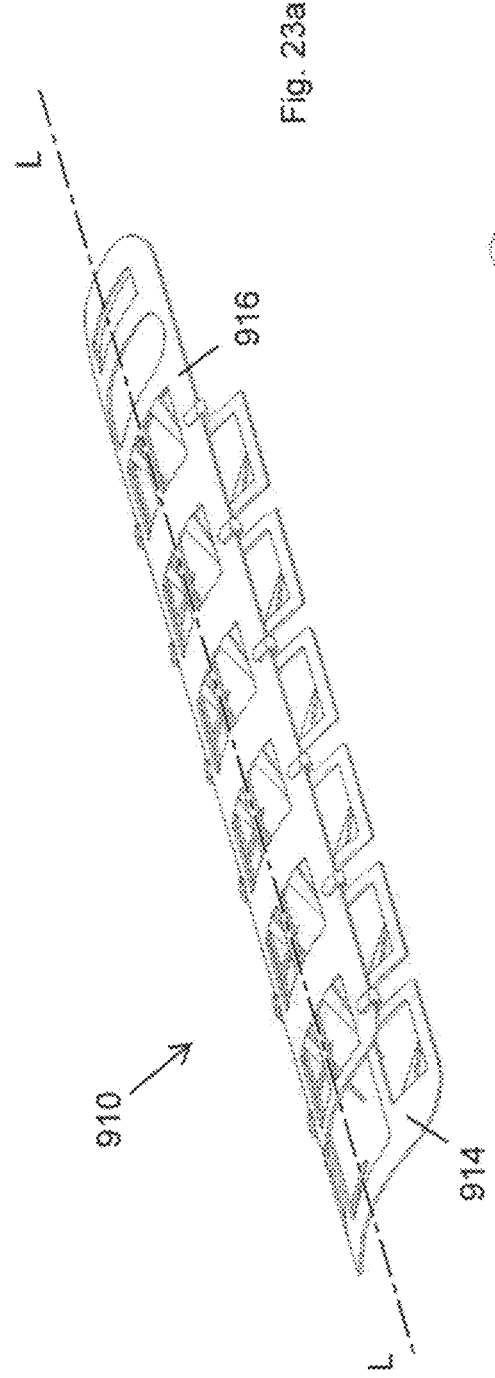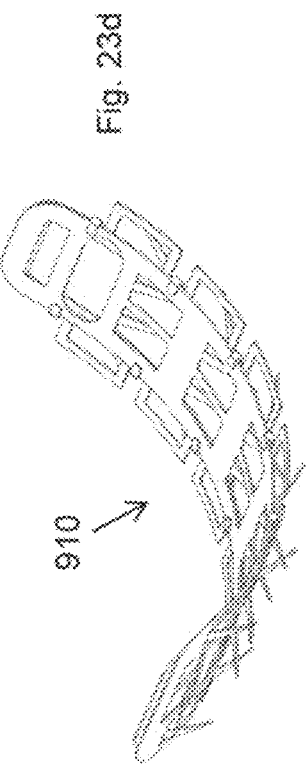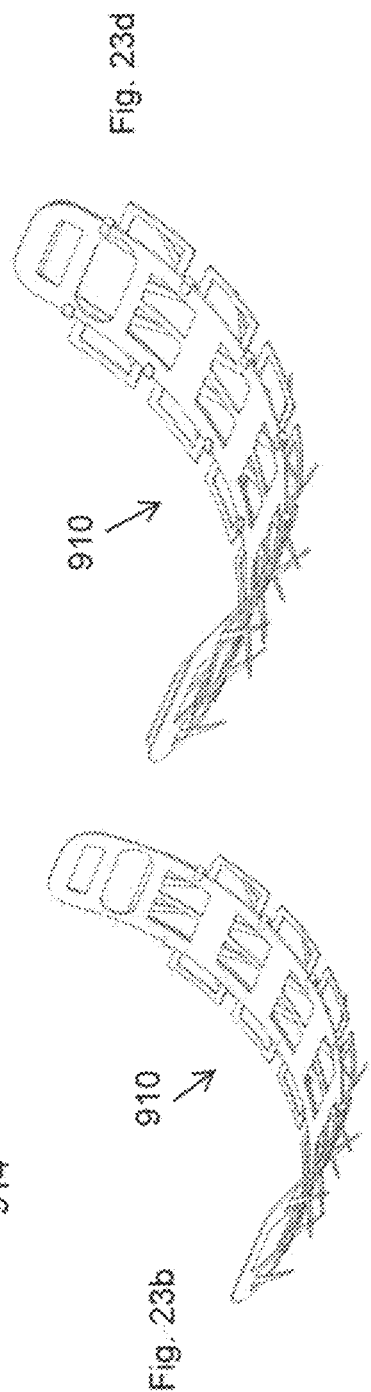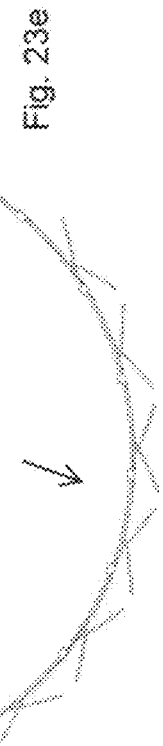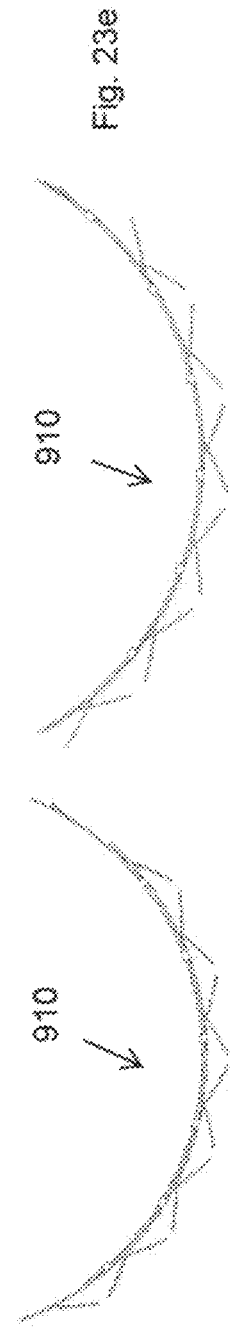

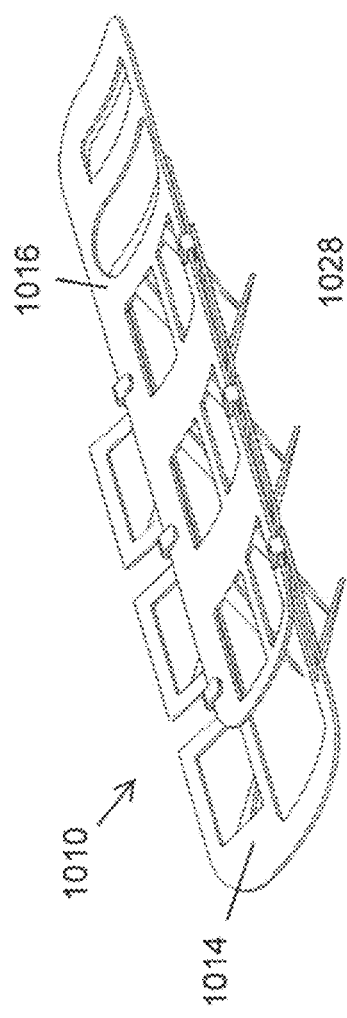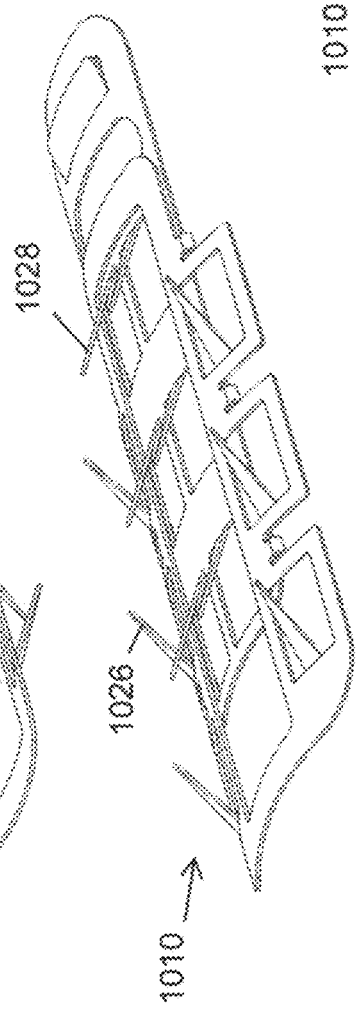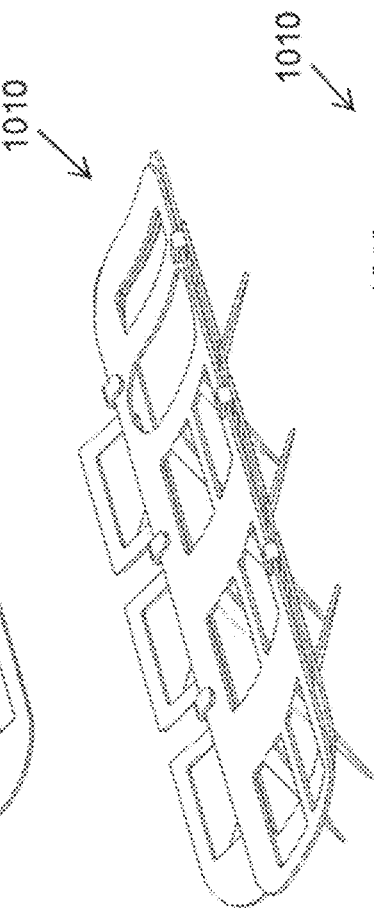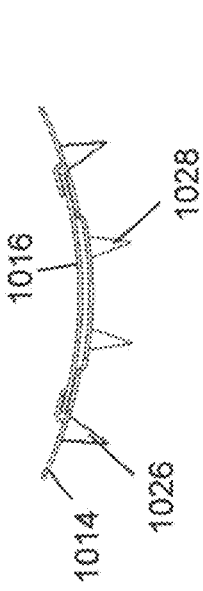

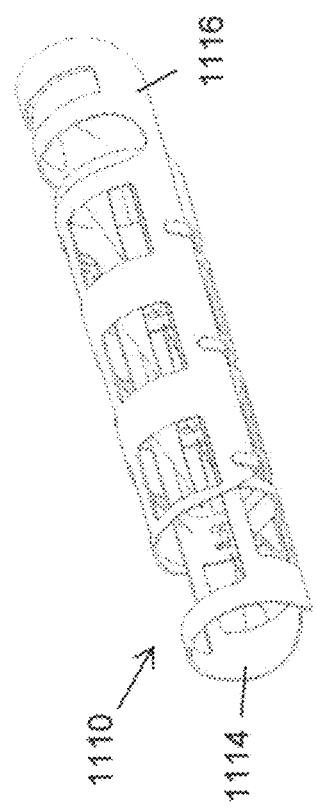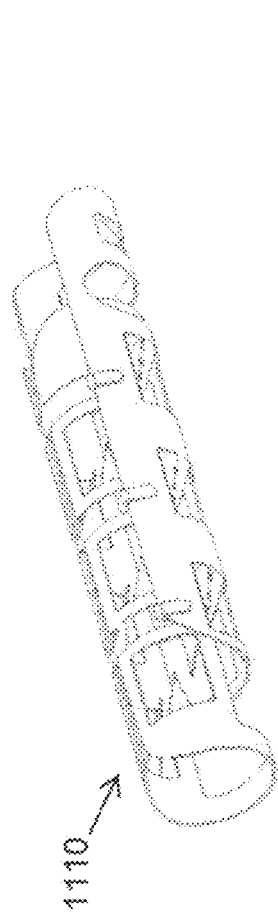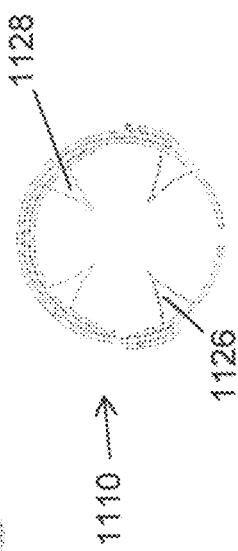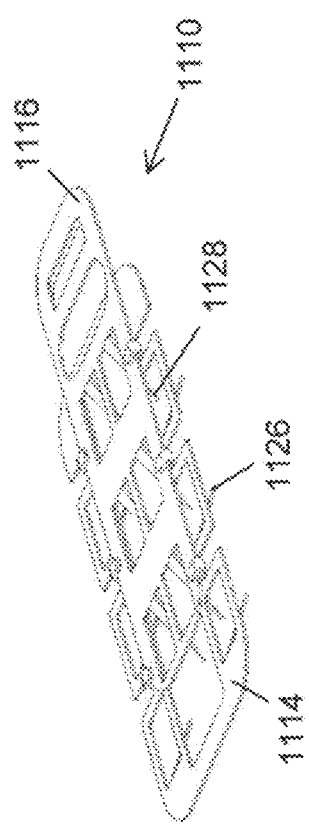

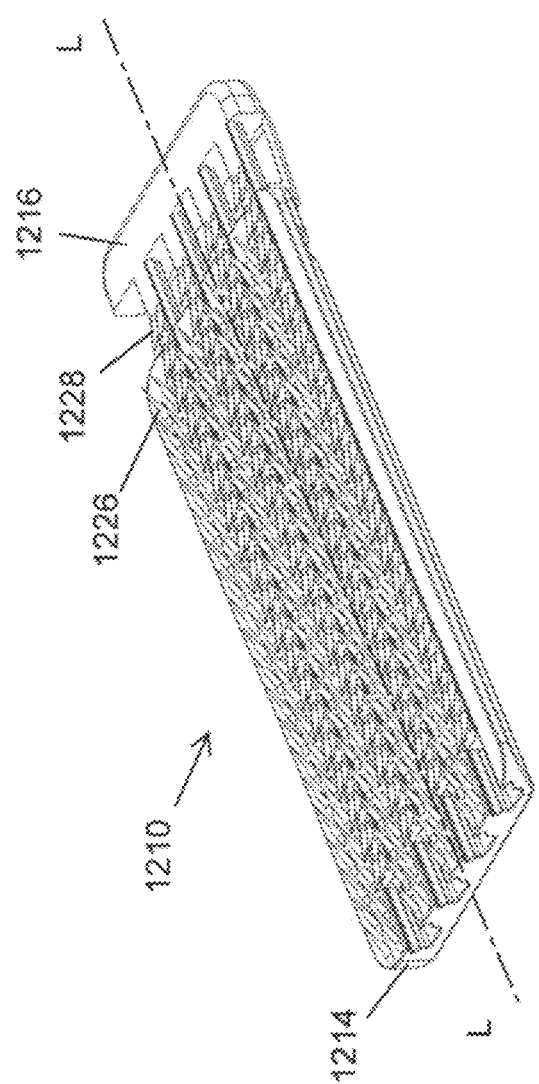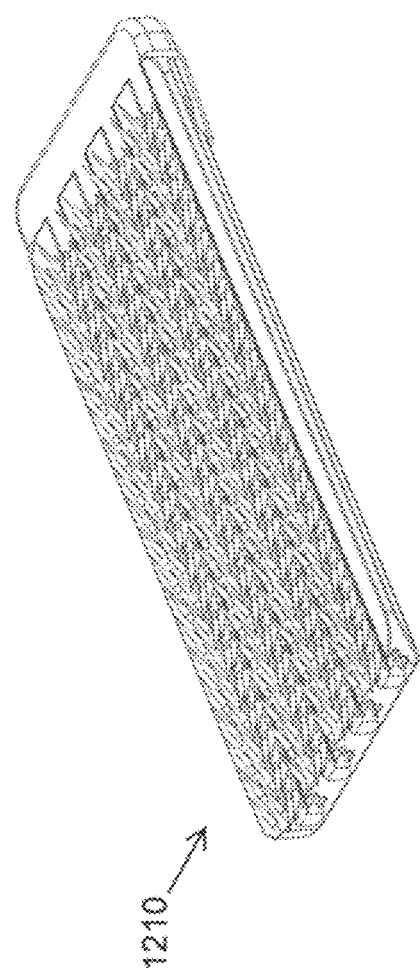

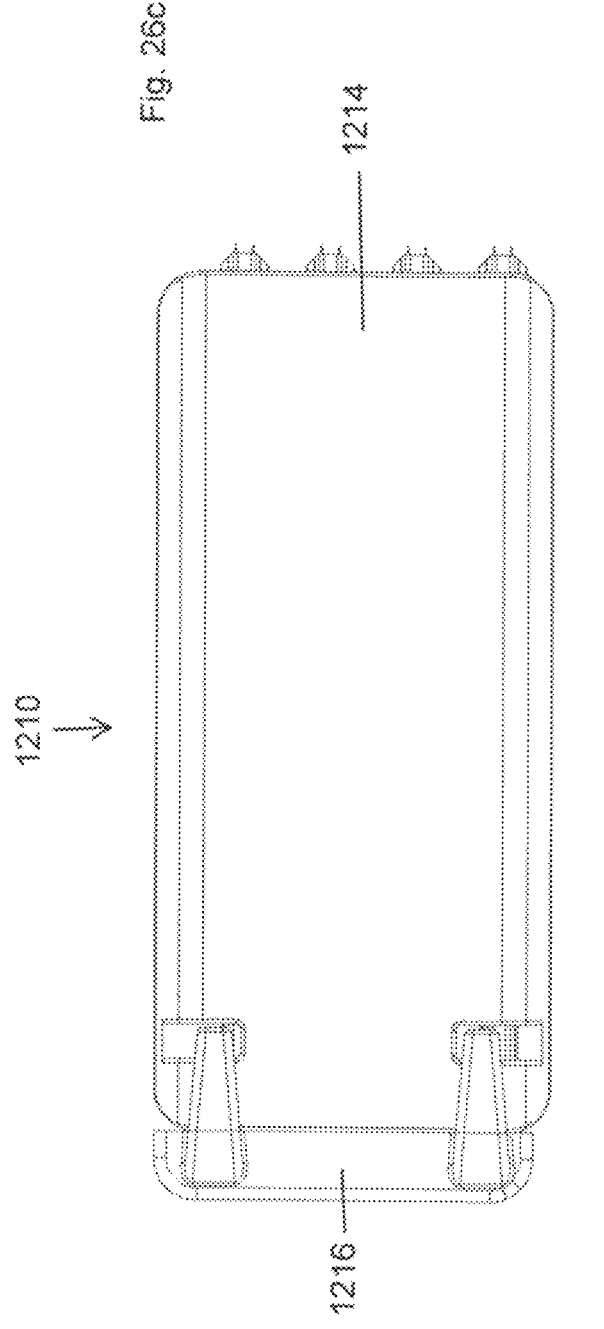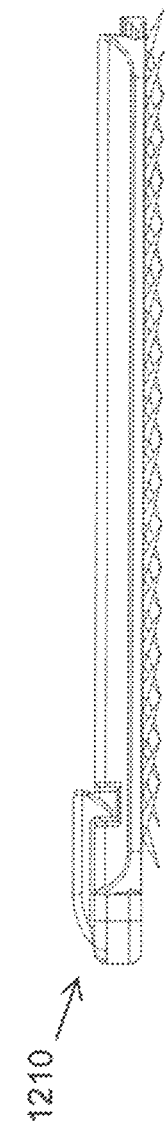

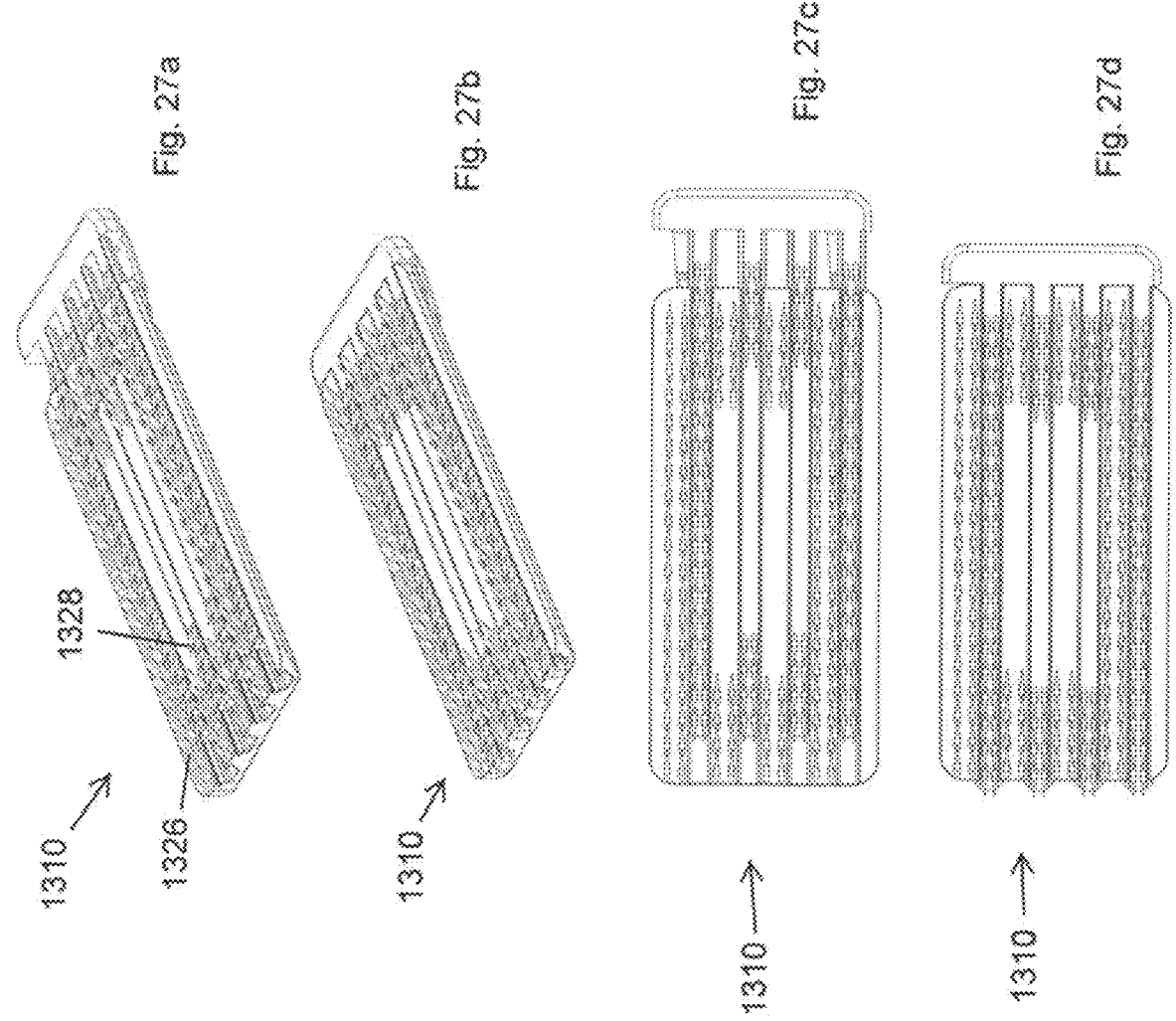

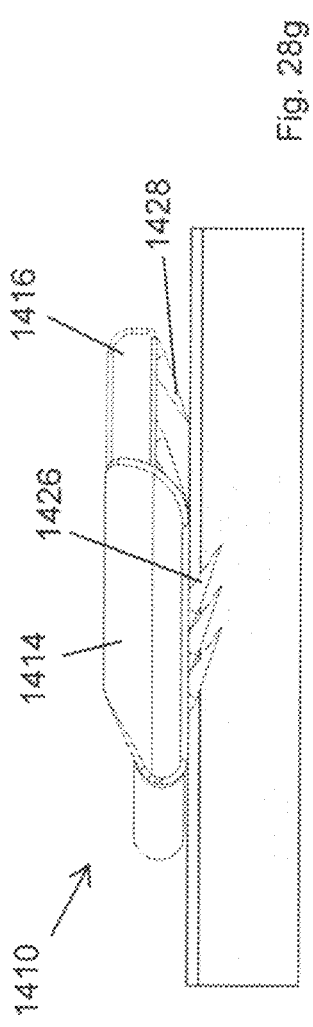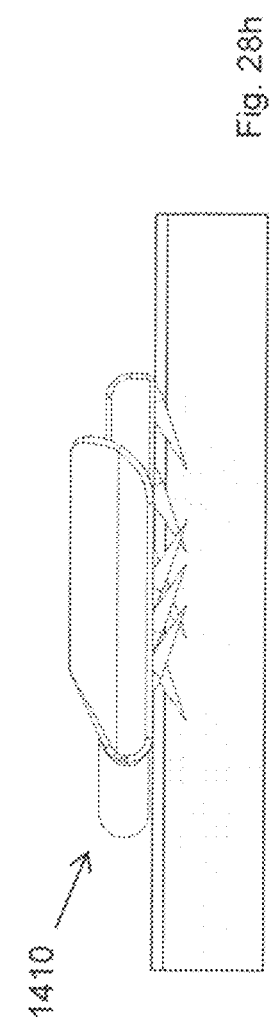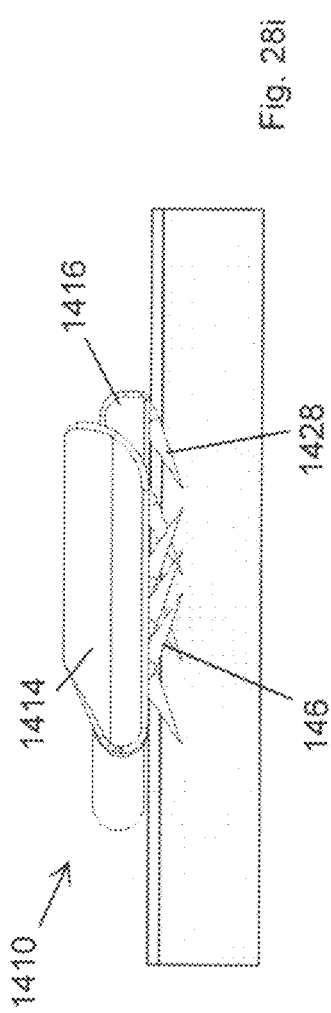

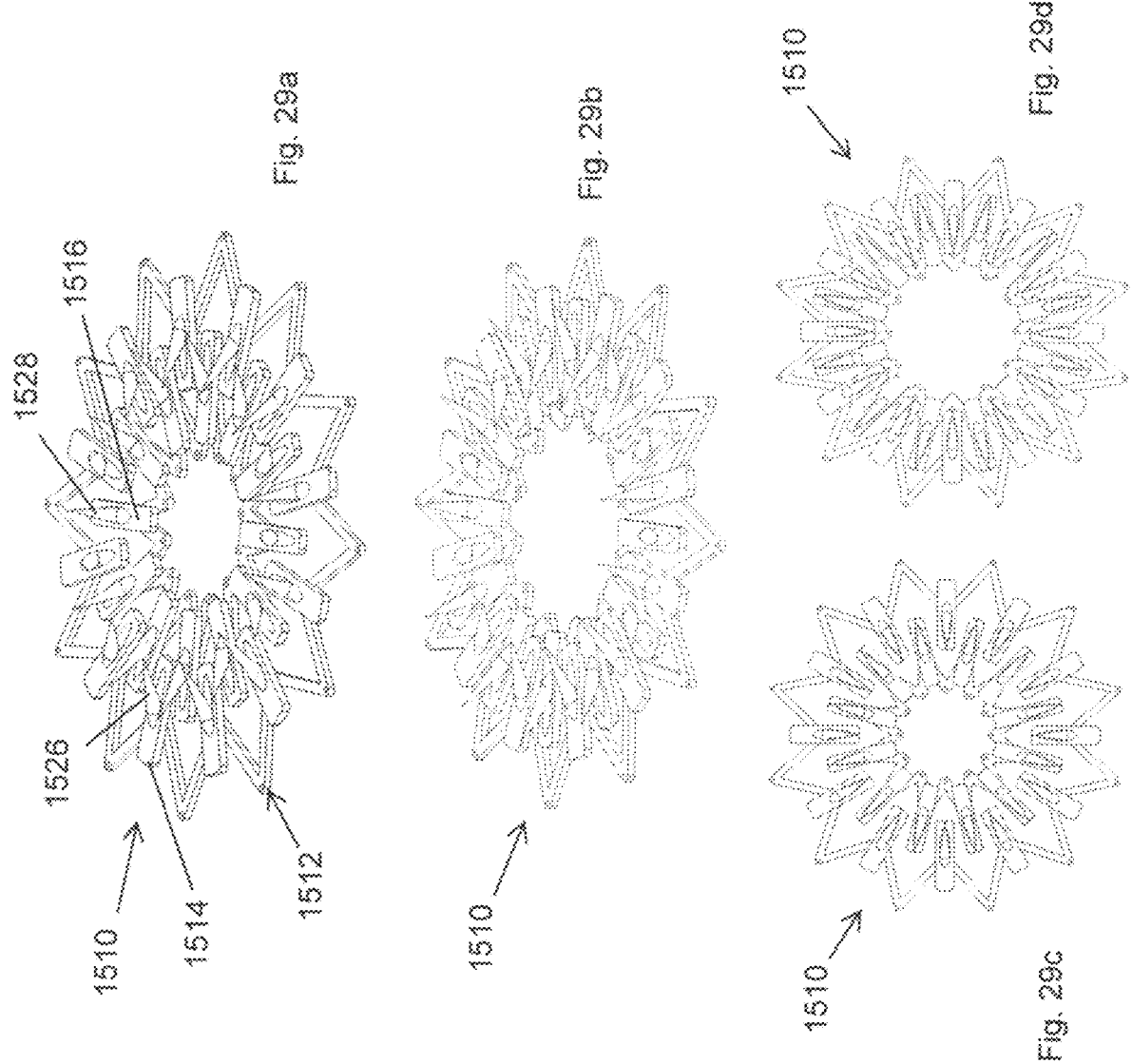

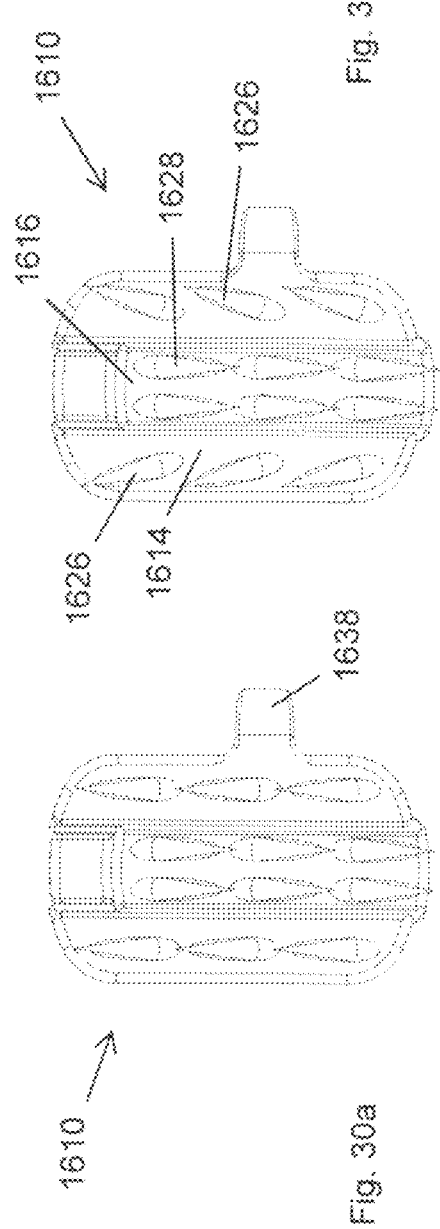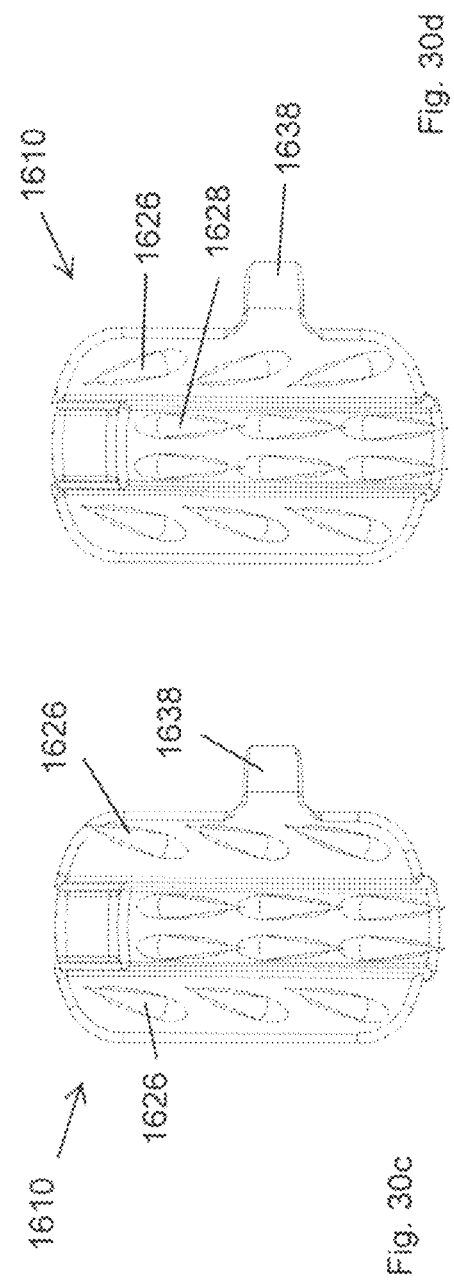

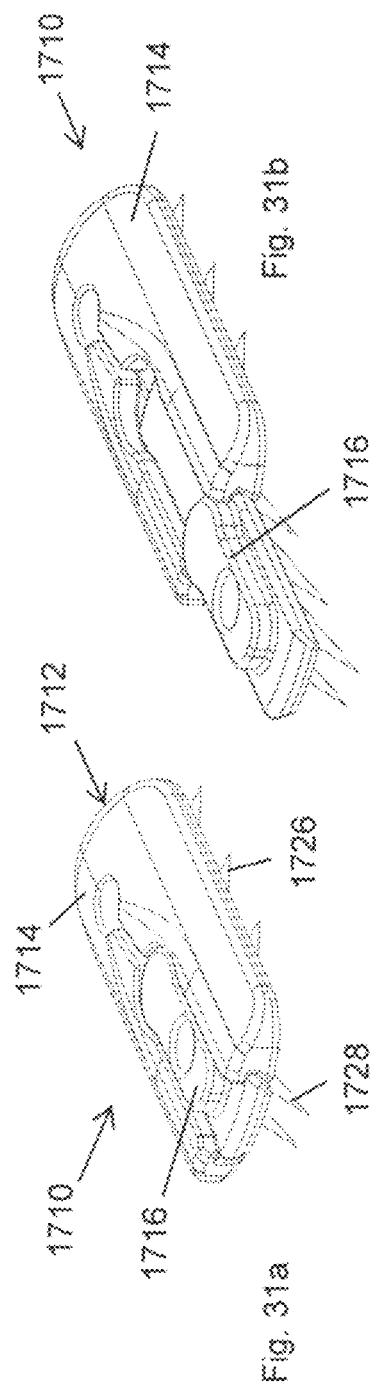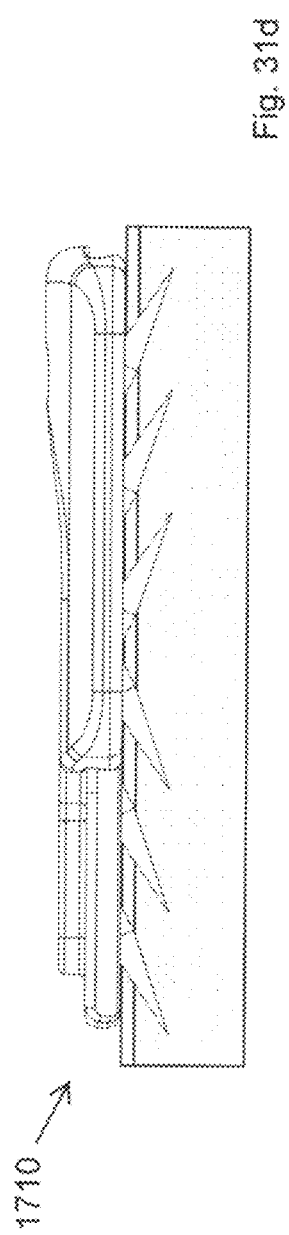
Fig. 31a Fig. 31b Fig. 31c Fig. 31d

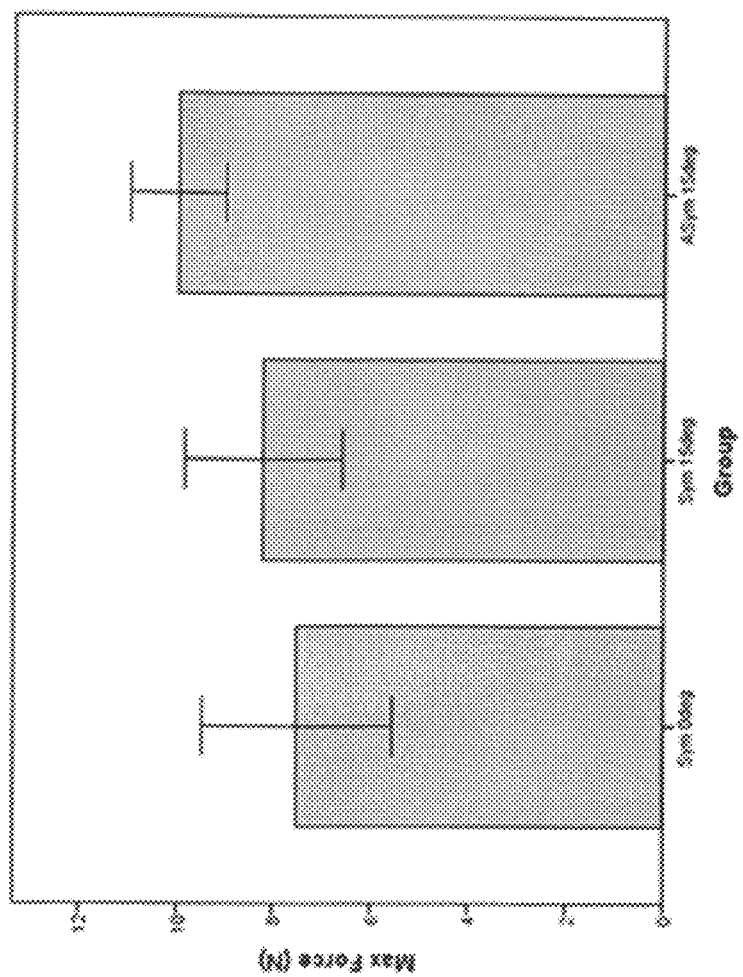

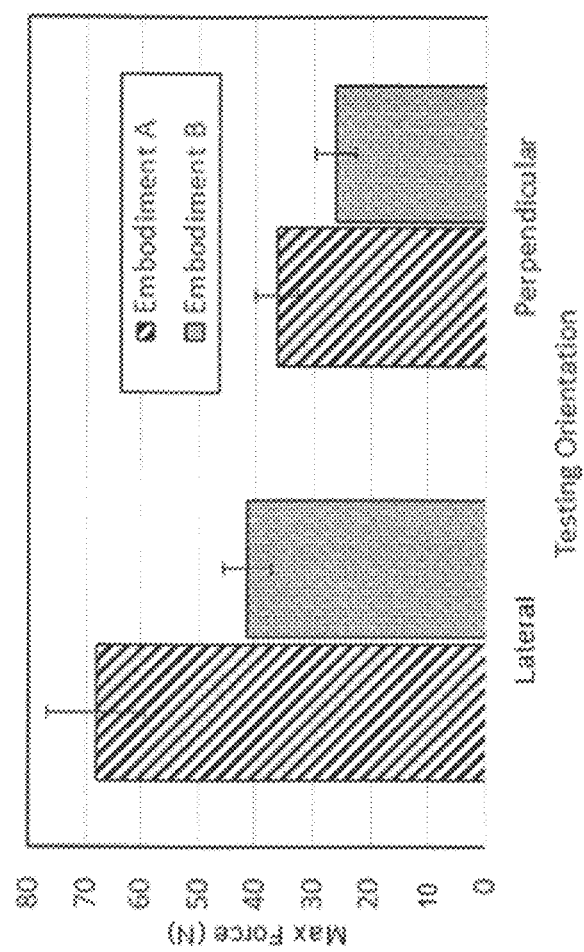

TISSUE ANCHOR

FIELD OF THE INVENTION

This invention relates to a tissue anchor that may be deployed in a wide range of tissues, including akin, dura, bowel, bladder, cardiac tissue, and arterial well, in addition to bone and cartilage. The tissue anchor can have multiple medical indications. These include bid are not limited to a wound closure system which may be used externally and internally.

In addition the anchor may be used to anchor therapeutic and diagnostic surgical and interventional devices to the skin. These include surgical catheters, drains, cannulae and stoma dressings. The anchor may be deployed utilising open and/or minimally invasive techniques including endoscopic and radiologically guided applications.

The anchor may also be used in applications such as hernia repair for securing a repair mesh at one or more sites, and reattachment of tissue structures including bone, tendon and labral repairs. The anchor may additionally be used for drug delivery, tattoo removal, bio-sensing and transcutaneous electrical nerve stimulation (TENS) applications, as well as measuring other bioelectrical activity in muscle tissue such as EMG and ECG.

BACKGROUND OF THE INVENTION

Across a wide range of surgical and medical procedures it is generally desirable to minimise tissue trauma, which is beneficial in both reducing surgical times and patient recovery, in addition to reducing the risk of infection, minimising the surgical equipment needed and thus potential the number of surgeons and/or support personal required to perform a given surgical or medical procedure.

As an example, sutureless wound closure devices and systems are being increasingly employed in the surgical closure of wounds Benefits to such systems include decreases in procedural time and patient time under sedation, scar reduction, reduced infection rates and improvements in cosmesis. Where staples and sutures are displaced by such systems, additional benefits are derived by obviating the need for the patient to return to the doctor's rooms or clinic once the wound has healed to have the staples and/or sutures removed. The downside to these systems is that they are, for the most part, reliant on adhesives to achieve attachment of the anchorage devices to the tissue surface. By their very nature the mechanical integrity of the adhesive bond can be compromised by local tissue composition and coatings. pH and moisture, emanating from the tissue or exudate from the wound itself. Furthermore, topical skin adhesives are known to be mechanically-inferior to suture repair and soft tissue anchors, as well as being associated with the potential for Allergic Contact Dermatitis and other Medical Adhesive Related Skin injuries.

Similarly, in tissue anchor applications, for example for Internal or external anchoring of a medical device, mesh, biosensor or the like, it is again beneficial to minimise tissue trauma while ensuring sufficient anchoring to the tissue, and to simplify the deployment of such tissue anchors to again reduce the time and effort required for deployment.

It is therefore an object of the present invention to provide an improved tissue anchor which may be used for multiple surgical and medical indications, for example wound closure applications or the like.

SUMMARY OF THE INVENTION

According to a first aspect of the present invention there is provided a tissue anchor comprising a body having a first section and a second section displaceable in a first direction relative to one another to translate the tissue anchor between an undeployed state and a deployed state: at least one protrusion projecting from the first section and at least one protrusion projecting from the second section, at least one protrusion on at least one section being inclined towards the at least one protrusion on the other section; and wherein the at least one protrusion on the first section and the second section overlap in a second direction substantially perpendicular to the first direction when the anchor is in the undeployed and/or deployed state.

Preferably, the body is configured such that the at least one protrusion on the first section and the second section overlap in the second direction when the body is in the deployed state.

Preferably, each protrusion comprises a root and a tip, each protrusion being aligned from the root to the tip in a direction substantial parallel to the first direction.

Preferably, each protrusion comprises a barb.

Preferably, the first section and the second section each comprise a plurality of protrusions.

Preferably, the find section and the second section comprise equal numbers of protrusions.

Preferably, the protrusions on both the first and second sections are arranged in a rectangular array.

Preferably, the protrusions on the first and the second section are arranged in concentric circular arrays.

Preferably, the protrusions comprise micro features.

Preferably, the first section and the second section each define a tissue contacting surface from which the respective at least one protrusion extends.

Preferably, the tissue contacting surface of fee first section and/or the second section comprises a recess located at or adjacent a root of the respective at least one protrusion.

Preferably, the first section comprises a first set of protrusions and a second set of protrusions spaced from the first set, the second section being displaceable relative to fee first section along a path between the first and second set of protrusion of the first section.

Preferably, one or more of fee protrusions on fee first section extend obliquely with respect to the first direction.

Preferably, the tissue anchor comprises a lock operable to fix the first and second sections relative to one another.

Preferably, the first section defines a channel adapted to at least partially receive fee second section therein.

Preferably, fee channel is open at one end.

Preferably, at least one of the protrusions comprises an electrically conductive material.

Preferably, a region of the body is devoid of protrusions.

Preferably, fee tissue anchor comprises a coupling provided on the body.

Preferably, the tissue anchor comprises at least one micro-needle.

Preferably, at least one of fee protrusions comprises a micro-needle.

Preferably, the tissue anchor comprising at least one biosensor.

Preferably, the body is at least partially formed from a bioresorbable material.

Preferably, the body is at least partially formed from a porous material.

Preferably, the first and second sections are reversibly displaceable relative to one another.

Preferably, the first and second sections are displaceable relative to one another in a direction substantially parallel to a longitudinal axis of the at least one inclined protrusion.

Preferably, the first and second sections are displaceable relative to one another along a substantially arcuate path.

Preferably, the body is displaceable between a furled and an unfurled state.

According to a second aspect of the invention there is provided a wound closure system comprising an array of the tissue anchors according to the first aspect of fire invention; and at least one tensile member tethered between at least two of the tissue anchors.

Preferably, the tensile member comprises a suture.

Preferably, the wound closure system comprises a template for locating the array of tissue anchors in a predetermined orientation.

Preferably, the array of anchors are arranged in at least two substantially parallel sets of anchors in which each anchor is oriented such that the first and second section are displaceable rotative to one another in said parallel direction.

According to a third aspect of fire present invention there is provided a method of securing a tissue anchor to tissue, the method comprising the steps of inserting at least one protrusion projecting from a first section of a body of fire anchor and at least one protrusion projecting from a second section of the body into the tissue; displacing in a first direction the first section relative to the second section to translate fire tissue anchor from an undeployed state to a deployed state, wherein the at least one protrusion on fee first section and the second section overlap in a second direction substantiality perpendicular to the first direction when the body Is in the undeployed and/or deployed state; such as to effect localised shear deformation of the tissue surrounding the protrusions when the body is in the deployed state.

Preferably, the at least one protrusion on the first section and the second section overlap in the second direction when the body is in the deployed state.

Preferably, the method comprises the step of locking me first section relative to me second section once the anchor is in the deployed state.

Preferably, the step of displacing the first section relative to the second section is effected in two stages, a first stage in which the relative displacement primarily effects insertion of the protrusions into the tissue, end a second stage which primarily effects the localised shear deformation of the tissue surrounding the protrusions.

Preferably, the method comprises deploying an array of the tissue anchors; and connecting at least one tensile member between at least two of the tissue anchors.

Preferably, the method comprises the steps of locating an array of the tissue anchors on either side of a tissue incision; and utilising the at least one tensile member in order to effect apposition of sides of the incision.

Preferably, displacement in the first direction comprises rectilinear and/or curvilinear displacement.

As used herein, the term "barb" is intended to mean a sharp or pointed protrusion or projection which is normally disposed at an angle to the object or surface from which it projects in order to reduce the likelihood of the barb disengaging from the substrate into which it is engaged.

As used herein, the term "micro feature" or "microneedle" is intended to mean a feature or needle/barb which is of a particular dimension, generally in the range of 100-3,000 micrometres (μm) in length or height, and may include for example a "microneedle" which can be used as a barb and/or as a combined barb and drug delivery or bio-sensing system.

BRIEF DESCRIPTION OF THE DRAWINGS

The present invention will now be described with reference to fire accompanying drawings, in which:

FIG. 1a illustrates a plan view from above of a tissue anchor according to a preferred embodiment of the invention in an un-deployed state;

FIG. 1b illustrates a side elevation of the tissue anchor of FIG. 1a in the un-deployed state;

FIG. 1c illustrates a plan view from below of the tissue anchor as shown in FIGS. 1a and 1b, again in the un-deployed state;

FIG. 2a illustrates a plan view from above of the tissue anchor of FIG. 1 in a deployed state;

FIG. 2b illustrates a side elevation of the tissue anchor of FIG. 1d;

FIG. 2c illustrates a plan view from below of the tissue anchor as shown in FIGS. 1d and 1e, again in the deployed state;

FIG. 3 illustrates a side view of the tissue anchor of FIGS. 1 and 2 in the un-deployed state on a section of tissue to which the anchor is to be secured;

FIG. 4 illustrates the tissue anchor of FIG. 3 having been partially deployed so as to draw an array of microneedles into the tissue;

FIG. 5 illustrates the tissue anchor of FIGS. 3 and 4 having been fully deployed such as to effect shear deformation of the tissue surrounding the microneedles of the anchor:

FIG. 6 illustrates a schematic perspective view of one of the microneedles of the tissue anchor of the invention;

FIG. 7 illustrates a schematic side elevation of the microneedle as shown in FIG. 6;

FIG. 8 illustrates a schematic perspective view of a microneedle of the tissue anchor of the invention and having an alternative cross-sectional shape when compared to that of FIG. 8;

FIG. 9 illustrates an array of the tissue anchors, each in the un-deployed state, arranged in an array about an incision or wound;

FIG. 11 illustrates the array of tissue anchors of FIG. 10 in which a suture has been deployed between the anchors, FIG. 12 illustrates the array of tissue anchors illustrated in FIG. 11 in which the opposed sides of the wound have been drawn together using the suture and anchors;

FIG. 13 illustrates a perspective view of a template carrying an array of the tissue anchors shown in FIGS. 1 to 8:

FIG. 14 illustrates a plan view of the template of FIG. 13;

FIG. 15 illustrates a plan view, from beneath, of a first alternative embodiment of a tissue anchor according to the present invention in an un-deployed state;

FIG. 18 illustrates a plan view, from beneath, of a second alternative embodiment of a tissue anchor according to the present invention, in an un-deployed state;

FIGS. 18a to 18f illustrate various views of a fourth alternative embodiment of a tissue anchor according to the present invention.

FIGS. 19a to 18d illustrate various views of a fifth alternative embodiment of a tissue anchor according to the present invention;

FIGS. 20a to 20e illustrate various views of a sixth alternative embodiment of a tissue anchor according to the present invention;

FIGS. 21a to 21d illustrate various views of a seventh alternative embodiment of a tissue anchor according to the present invention;

FIGS. 22a to 22d illustrate various views of an eighth alternative embodiment of a tissue anchor 25 according to the present invention;

FIGS. 23a to 23e illustrate various views of a ninth embodiment of a tissue anchor according to the present invention;

FIGS. 24a to 24d illustrate various views of a tenth embodiment of a tissue anchor according to the present invention;

FIGS. 25a to 25d illustrated various views of an eleventh embodiment of a tissue anchor according to the present Invention;

FIGS. 26a to 28d illustrate various views of a twelfth embodiment of a tissue anchor according to the present invention;

FIGS. 27a to 27d illustrate various views of a thirteenth embodiment of a tissue anchor according to the present invention, being a modified version of the twelfth embodiment:

FIGS. 28a to 28g illustrate various views of e fourteenth embodiment of a tissue anchor according to the present invention;

FIGS. 29a to 29d illustrate various views of a fifteenth embodiment of a tissue anchor according to the present invention;

FIGS. 30a to 30d illustrate various views of a sixteenth embodiment of a tissue anchor according to the present invention;

FIGS. 31a to 31d illustrate various views of a seventeenth embodiment of a tissue anchor according to the present invention;

FIG. 32 illustrates the results of tests carried out on a number of prototype tissue anchors produced for testing purposes;

FIG. 33 illustrates the results of a mechanical test procedure being carried on a tissue anchor according to the present invention;

DETAILED DESCRIPTION OF THE DRAWINGS

Figure 10:
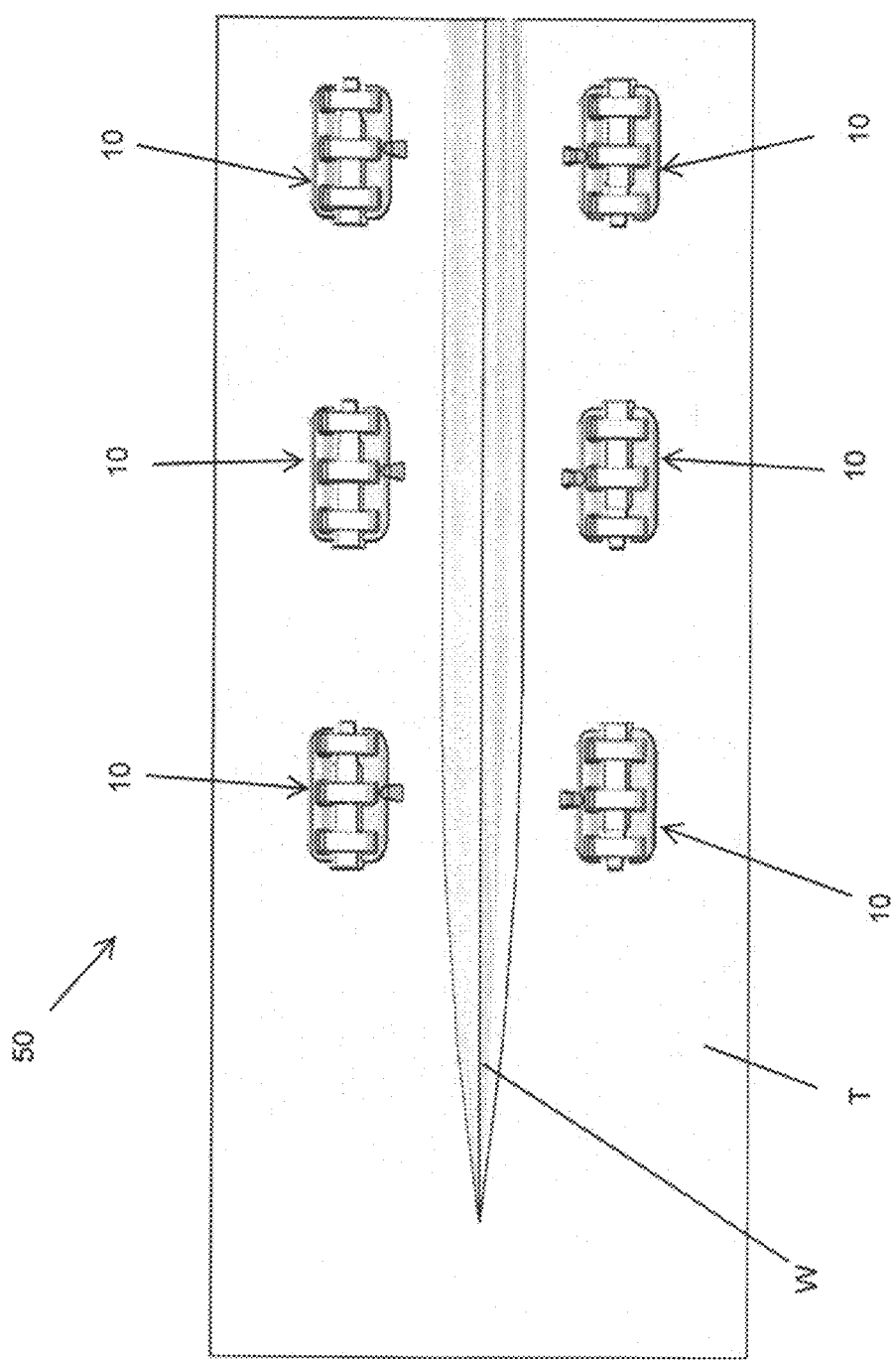
FIG. 10 illustrates the arrangement of FIG. 9 in which the tissue anchors have been displaced into the deployed state.
Figure 17B:
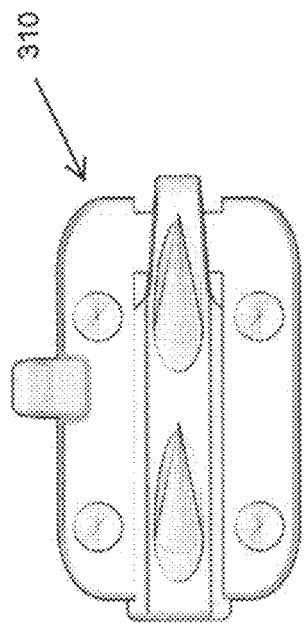
FIGS. 17a to 17d illustrate various views of a third alternative embodiment of a tissue anchor according to the present invention.
Figure 17D:
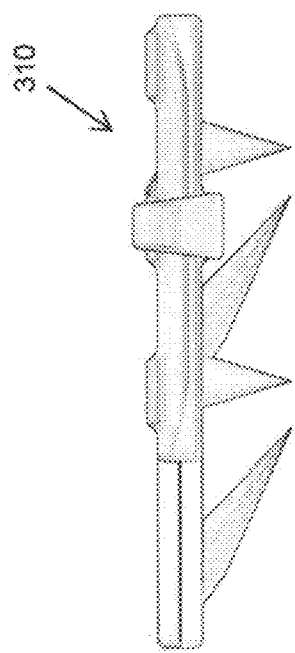
Figure 17A:
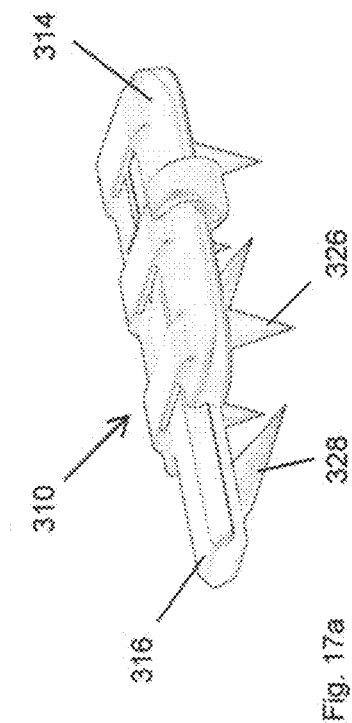
Figure 17C:
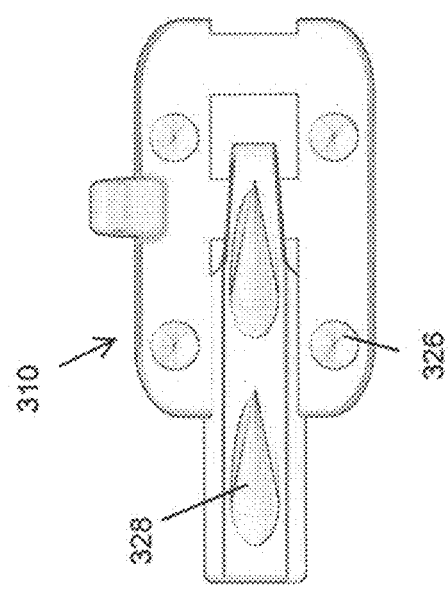

Referring now to FIGS. 1 to 7 of the accompanying drawings there is illustrated a tissue anchor according to a preferred embodiment of the present invention, generally indicated as 10, for use in various surgical, medical and diagnostic indications, in particular being suited to wound closure applications such as incisions in the skin, dura mater, blood vessels, bowel wait or any other tissue located internally or externally of the body. In addition, the anchor may be used to facilitate attachment of surgical and Interventional devices (not shown) to adjacent tissue at a desired location, and reattachment of tissues following injury. The tissue anchor 10 may be used with tissue, bone, or any other suitable biological substrate, and may be used in applications such as drug delivery, as or for securing a biosensor, and transcutaneous electrical nerve stimulation (TENS) and/ or measurement of electrical activity in tissue such as muscle, otherwise known as electromyography (EMG) and electrocardiography (ECG).

The (issue anchor 10 comprises a body 12 which may be formed of any suitable material, for example a polymer, metal or a composite of materials, and may for example comprise a bioabsorbable material or a material which is partially or wholly porous in order to promote tissue ingrowth. Although not limited to particular dimensions, in the exemplary embodiment illustrated the body 12 has a length in the region of 9 mm as measured along a longitudinal axis LL, a width in the region of 6 mm as measured perpendicular to the longitudinal axis LL, and a thickness in the region of 2.5 mm perpendicular to both the length and width. These dimensions may of course vary, in particular to suit particular surgical indications. For ease of reference, hereinafter measurements along the length will be referred to as being an "X" coordinate, measurements along the width will be referred to as being a "Y" coordinate and measurements along the depth will be referred to as being a "Z" coordinate.

The body 12 comprises a first section 14 and a second section 15 which are displaceable relative to one another in a first direction and between an undeployed state as illustrated in FIGS. 1a,b,c and a deployed slate as illustrated in FIGS. 2a,b,c, and as will be described in greater detail hereinafter. The first section 14 and the second section 16 are inter-engagable with one another, and in the embodiment illustrated the first section 14 defines a central channel 18 extending longitudinally from an open end of the body 12 to terminate at a closed end 20 which serves to bridge and thus join the opposed portions of the first section 14, on either side of the channel 18, to one another. Thus, in the embodiment illustrated the first section 14 can be said to be substantially C or U shaped. The second section 16 is shaped and dimensioned to be slidingly received within the channel 18, the second section 16 preferably being provided with a key 22 along either lateral side white the side walls of the channel 18 are each provided with a corresponding keyway 24 therein. It wifi of course be appreciated that any other suitable arrangement or configuration may be employed in order to permit relative movement between the first section 14 and the second section 16. While in the embodiment illustrated the first and second sections are reversibly displaceable relative to one another, in other embodiments the displacement may be irreversible.

Both the first section 14 and the second section 16 each comprise at least one protrusion, and preferably a plurality of the protrusions in the form of six barbs or microneedles 26 projecting from the first section 14 and six barbs or microneedles 28 projecting from the second section 16. In each case the barbs 26, 28 extend from an underside or tissue contacting surface 30 of the respective first section 14 and second section 16. Each of the barbs 26, 28 comprise a root 32 which is defined at the tissue contacting surface 30 and a sharpened or pointed tip 34 at a free end of the respective barb 26, 28. In the preferred embodiment the barbs 26, 28 taper uniformly from root 32 to tip 34 although any other suitable configuration may be employed. The uniform taper has however been found to be beneficial in facilitating insertion of the barbs 26, 28 folly into tissue as hereinafter described in detail.

The barbs 26, 28 are inclined at an acute angle α relative to the "X" plane in which the tissue contacting surface 30 lies and extend predominantly in the same direction, from root 32 to lip 34 along a major axis of the barb 26, 28, as the direction of relative movement between the first section 14 and the second section 16, also referred to as the "first" direction substantially parallel to the longitudinal axis LL of the body 12. In other words the barbs 26, 28 can be said to have a greater "X" dimension component than "Z" dimension component.

The barbs 26, 28 are preferably in the form of so called "microneedles" which are dimensioned, in the preferred embodiments illustrated, with an axial length L from root 32 to tip 34 of approximately 2 mm and a depth or "Z" coordinate length, hereinafter referred to as $L_z$, of approximately 0.9 mm. It has also been found that the preferred angular inclination α of the barbs 26, 28 is between 15° and 50°, more preferably between 20° and 30°, and most preferably approximately 26.5° to the "X" plane. Both the "X" coordinate length $L_x$ and the "Z" coordinate length $L_z$ of each barb 26, 28 will vary depending on the angular inclination thereon. It will of course be appreciated trial all of these dimensions are exemplary and may vary, in particular to sun different surgical or medical applications or tissue types. The dimensions of barbs 26 and 28 could also vary across any given part. For example, those at the perimeter could be shorter in length than those at the centre, or vice versa. Similarly, barb lengths and aspect ratios could vary in multiple planes.

The barbs 26, 28 are arranged and oriented such that the barbs 26 protruding from the first section 14 extend in a direction generally opposite to that of the barbs 28 protruding from the second section 16. In this way the barbs 26 essentially face or oppose the barbs 28. It is also preferable that at least one of the barbs 26 overlaps with at least one of the barbs 26 in the "Y" direction, at least when the tissue anchor 10 is in either the deployed and/or un-deployed state, but most preferably when in the deployed state. In addition, it has been found that the greatest anchorage is achieved when the first and second sections 14, 16 have an equal number of barbs 26, 28. In the embodiment illustrated the first and second sections 14, 16 each comprise six barbs 26, 28, although this number may of course vary. The barbs 26, 28 are preferably spaced from one another in the "X" direction such that the tip 34 of any one barb 26, 28 just reaches or may slightly overlap with the root 32 of the adjacent barb 26, 28 or in other words the barbs are arranged linearly with a spacing between adjacent herbs 26, 28 of approximately $L_y$. In the preferred embodiment the "Y" spacing between the row of barbs 28 on the first section 14 and the adjacent row of barbs 28 on the second section is preferably 1.5 times the "Y" spacing between barbs 28 of the second section 16. This distance has been found to be effective in avoiding shear damage to the tissue engaged by the tissue anchor 10 in use. The distance that the first and second sections 14, 16 are displaced relative to one another between the undeployed and deployed states is preferably 2.5 times $L_x$, but could also for example be 2 times $L_x$ or less.

The barbs 26, 28 are arranged to penetrate at least an upper layer or region of tissue T to which the anchor 10 is to be secured, initially by pressing the tissue contacting surface 30 of the body 12 downwardly onto the anchorage site on the tissue in order to push the barbs 26, 28 into the tissue in a minimally invasive manner. The tissue anchor 10 is applied to the anchor site in the un-deployed state as illustrated in FIG. 3. Once the barbs 26, 28 are engaged against the tissue T the first and second sections 14, 16 are displaced relative to one another into a partially deployed state as illustrated in FIG. 4. The initial relative displacement of the first and second sections 14, 16 from the un-deployed to partially deployed states results in the barbs 26, 28 being drawn into the tissue as shown in FIG. 4. The distance of this rotative displacement is preferably 2 time $L_x$, such that the full length of the barbs 26, 28 is drawn into the tissue T. At this point the barbs 26, 28 are fully inserted into the tissue, and the first and second sections 14, 16 are then further displaced into the folly deployed state as shown in FIG. 5, which final movement causes the non-destructive shear deformation of the tissue engaged by the barbs 26, 28, for example the collagen network in the case of skin, effectively creating a localised resilient deformation which actively engages the tissue and the barbs 26, 28 in order to achieve a robust anchorage to the tissue and which is capable of resisting forces in multiple planes as hereinafter described. The distance of this final displacement is preferably 0.5 times $L_x$, with the understanding that these distances may of course be varied as required. This distance has been found to provide sufficient shear deformation of the tissue surrounding or acted on by the barbs 26, 28 to provide the requisite levels of retention while avoiding any damage to the tissue T.

Referring to FIGS. 6 and 7 the tissue anchor 10 may comprise recesses 35 formed in the tissue contacting surface 30, one directly beneath each of the respective barb 26, 28. The recesses 35 facilitate improved anchorage of the first and second sections 14, 16 to the tissue by allowing at least some of the tissue that is displaced by insertion of each barb 26, 28 to be received within the respective recess 35, thereby allowing a more complete insertion of each of the barb 26, 28. The recess 36 also effectively increases the overall or working length L of each barb 26, 28, but exposing the full root 32 which would otherwise be partially encased below the tissue contacting surface 30, The volume of tissue contained, in use, in each recess 35 also serves to resist lateral displacement of the anchor 10 as the tissue is effectively meshing or interlocking with the body 12. The dimensions of the recess 35 may be varied. FIG. 7 shows a barb or microneedle 26, 28 having a circular cross sectional area, while FIG. 8 shows an alternative barb or microneedle 26, 28 having a triangular cross sectional area. It should therefore be understood that various other alternative cross sectional areas may be employed for the barbs 26, 28.

In addition, white the embodiment described has a tissue contacting base, an alternative embodiment is envisaged in which elongated microneedles exhibit a step change in their diameter, which then effectively defines the tissue contacting surface and a hard shoulder for preventing further advancement of the microneedles into the tissue. In this way, the body could sit in an elevated position relative to the outer tissue layer, and which could be advantageous for drug delivery, as in a patch-and-poke application.

In order to retain the first section 14 and second section 18 in the deployed state the tissue anchor comprises locking means in the form of a substantially circular tab 36a formed at an upper face of the second section 18 which slides within the channel 18, and a correspondingly shaped and dimensioned socket 36b formed at the closed end of the channel 18 which receives and retains the tab 36a when the second section 16 is displaced fully into the first section 14, for example as illustrated in FIG. 2a. The socket 38b has a diameter slightly greater than the width or "Y" dimension of the channel 18 such that the point at which the channel 18 enters the socket 36b defines a slight restriction to entry of the tab 36a. In this way as the tab 36a is initially pressed into the channel 18 when replacing the first and second sections 14, 16 relative to one another the opposed portions of the first section 14 will be forced to resiliently deform away from one another in the "Y" direction in order to allow the channel 18 to accommodate the slightly wider tab 36a. This resilient deformation displaces the barbs 26 of the first section 14, which may have the effect of increasing the efficiency of microneedle insertion and embedding. The tab 36a then travels along the channel 18 before reaching and entering the socket 38b, at which point the resilience of the first section 14 reverts the channel 18 to the normal size thereby retaining the tab 36a in the socket 36b. This process can be reversed if necessary in order to release the tissue anchor 10, Thus the tab 36a and socket 36b serves as a simple yet effective means of locking the second section 16 relative to the first section 14 in order to retain the tissue anchor 10 in the deployed state. It will be understood by a person of ordinary skill in the art that the tab 36a and socket 36b could be replaced with any other functional alternative operable to, preferably reversibly, lock the first and second sections 14, 16 relative to one another.

It will be appreciated that due to the relatively email dimensions of the tissue anchor 10, in order to effect the displacement of the first section 14 relative to the second section 16 the body 12 may be provided with a pair of depressions 37a, 37b on the upper face, one on each of the first and second sections 14, 16, which may engaged by a tool (not shown) such as a needle nose pliers or the like, whose tips can be used to manipulate the first and second sections 14, 16 between the undeployed and deployed states. If will also be understood that any other suitable functional alternative may be employed to achieve this action.

By providing the opposed sets of barbs 26, 28 the local region of tissue on which the anchor 10 is deployed is effectively captured and lightly compressed and stretched between the overlapping barbs 26, 28 to order to apply shear deformation and thereby robustly secure the tissue anchor 10 in position. In particular when the tissue anchor 10 is displaced into the deployed state the local region of tissue beneath the body 12 is elastically deformed or compressed and stretched by the displacement of the first section 14 relative to the second section 16, and thus by displacement of the barbs 26 relative to the preferably overlapping barbs 28. This elastic shear deformation of the tissue results in a reactive force being applied by the tissue against the barbs 26, 28 thereby actively engaging and retaining the tissue surrounding the barbs 26, 28. As a result the barbs 26, 28 do not need to penetrate to a significant depth to achieve the necessary retention, and may for example be of a length in the region of 0.1-5 mm from root 32 to tip 34, and have a depth of penetration $L_z$ of less than 1000 μm, although again this dimension may be varied as required. As a result, for skin based indications, the barbs 26, 28 can be dimensioned such as not to penetrate to the depth of most pain receptors and Wood vessels. The reduced size of the barbs 26, 28 is further advantageous to surgical wound closure indications where penetration of the full thickness of tissue is contra indicated, such as in the repair of dural tears and durotomies.

Once engaged in position on tissue or other substrate the tissue anchor 10 can be used as an anchor point via which various functions may be performed, for example anchoring a suture, a surgical mesh, a biosensor, and any other suitable surgical or medical devices or systems. In addition the tissue anchor 10 may be provided with one or more micro needles (not shown) in order to permit the tissue anchor 10 to be used as a drug delivery system, it is also envisaged that one or more of the barbs 26, 28 could double as these microneedles, whereto the barb 26, 28 could include one or more lumens to facilitate drug delivery into the tissue penetrated by the barb 26, 28. Similarly one or more of the barbs 26, 28 may be utilised to effect transcutaneous electrical nerve stimulation (TENS) and/or measurement of electrical activity in tissue such as muscle, otherwise known as electromyography (EMG) and electrocardiography (ECG). In such applications the one or more barbs 26, 28 are formed from or coated with an electrically conductive material, preferably metal. As toe barbs 26, 28 penetrate into the tissue the anchor 10 will provide an improved electrical signal measurement over conventional surface based systems, and in addition repeated measurements are of improved accuracy due to the fixed position of the anchor 10 on the tissue.

In addition, in order to assist in displacement from the undeployed to the deployed state, the tissue anchor 10 may comprise biasing means (not shown), for example a simple spring or the like, arranged to act between the first and second sections 14, 16 in order to urge the first and second sections 14, 16 into full engagement with one another.

In a preferred indication the tissue anchor 10 is employed in an array to form a wound closure system 50 as illustrated in FIGS. 9-12. For such an application each of the tissue anchors 10 compose at least one eyelet 38 provided on or formed integrally with the body 12, preferably with the first section 14 and located outboard of the body 12 for ease of access by a surgeon. It will of course be appreciated that the number and/or position of the eyelet 38 may be varied as required. In addition the eyelet 38 could be replaced with any other functional alternative coupling adapted to tether or otherwise secure suture or the like to the anchor 10, for example a strangulation type coupling. In the embodiment illustrated the eyelet 38 is provided along one lateral edge of the first section 14. The tissue anchors 10 are deployed onto the skin or other tissue T about an incision or wound W, with a set of the tissue anchors 10 being provided on either side of the wound W. Each of the tissue anchors 10 is oriented such that the longitudinal axis LL thereof is aligned substantially parallel to the major axis of the wound as illustrated. The anchors 10 could however be deployed with the longitudinal axis LL arranged substantially perpendicular to the wound W, in which case the eyelet 38 would preferably be repositioned onto the shorter side of the body 12 and thus facing the wound W.

The anchors 10 are applied to the tissue in the undeployed state as illustrated in FIG. 9 with the eyelet 38 of each anchor 10 preferably facing the wound W. Thus the anchors 10 on one side of the wound are arranged in reverse orientation to those on the opposed side of the wound W. Once positioned on the tissue T with the barbs 26, 28 penetrating the tissue T the anchors 10 are then displaced into the deployed state by sliding the second section 16 relative to the fast section 14, as illustrated in FIG. 10. This actively secures each of the tissue anchors 10 in position, at which point a tensile member in the form of a suture S is threaded through the eyelet 38 of a first anchor 10 and then across the wound W to the opposed anchor 10, before being threaded obliquely back across the wound W to the anchor 10 adjacent the first threaded anchor 10, and so on, until the foil array of tissue anchors 10 have been captured by the sutures. Tension is then applied to the suture S in order to draw the opposed sides of the wound W into apposition as illustrated in FIG. 12, and foe suture S is then suitably secured in order to hold the wound W in the closed position. The active retention of each of the anchors 10 by virtue of the localised deformation of the tissue T between the opposed sets of barbs 26, 28 ensures that each anchor 10 can resist forces in multiple planes to ensure that each anchor 10 remains in position while resisting the force being applied by the tensioned suture S.

Referring now to FIGS. 13 and 14, in order to simplify the process of deploying the array of tissue anchors 10 the wound closure system 50 may comprise a template 60 which is adapted to retain me array of tissue anchors 10 in predefined positions and orientations and which template 80 can then be applied to the tissue T as a single component and thus in a single step. The template 60 may for example comprise a simple rectangular or other shaped frame 70 to which each of the tissue anchors 10 is secured, for example by a frangible element 80 designed to be quickly and easily broken or otherwise disconnected from the frame 70 and/or tissue anchor 10 once aft of the tissue anchors 10 are engaged with the tissue T.

In order to further simplify the deployment process for the wound closure system 50 the suture S as described above may be preinstalled between the various tissue anchors 10 in a predetermined configuration such that as soon as the tissue anchors 10 are released from the frame 70 the suture S can be tensioned in order to effect closure of the wound W.

In an alternative methodology the wound closure system 50, with or without the template 60, may be pre-deployed about the site of a proposed incision to be made as part of a surgical procedure, such that as soon as the procedure is completed the closure system 50 may be immediately utilised to close the incision. Thus in addition to reducing the time taken to perform a surgical procedure, the closure system 50 will also act as a means of accurately realigning the opposed sides of the incision to their pre-incision positions relative to one another, thereby significantly improving the cosmetic outcome. Ideally, each row of anchors 10 wifi have an interlinking member (not shown) which serves to prevent loss of an anchor 10 through the surgical window whilst the wound is open.

Alternatively the wound closure system 50 may comprise a template in the form of a flexible polymer sheet {not shown} or the like provided with an adhesive on an underside of the sheet and to which the array of tissue anchors 10 are fixed in a predetermined arrangement, for example the two dimensional matrix shown in FIGS. 9-12, in use the surgeon will place the sheet incorporating the tissue anchors 10 onto the surgical site, adhering the sheet to the skin or other tissue such that the anchors 10 are deployed in the two evenly spaced rows about the planned incision site. With the anchors 10 so located and in the deployed state the surgical incision may then be made and the polymer sheet peeled from the tissue, leaving the anchors 10 in place. Again at the completion of the surgical procedure the surgeon can then manipulate and approximate the wound edges achieving closure using the tensioned suture S as described above, or any other suitable tensile member or bridging element (not shown) extending between anchors 10 across the wound W. It is also envisaged that the tissue anchors 10 may be individually provided on an adhesive tape or strip (not shown) in order to aid in the deployment of the anchor 10.

In order to further facilitate the expedient and accurate closure of such wounds various aspects of the tissue anchors 10 and wound closure system 50 may be modified. For example as mentioned above the array of tissue anchors 10 may be preloaded with a suture or functionally alternative tensile members or bridging elements (not shown) extending between the opposed rows of tissue anchors 10. The position of the eyelet 38 on the body 12 may be adjustable in order to improve approximation of the wound margins. Additionally or alternatively the suture may be provided with Knot like nodes at predetermined intervals along the length of the suture in order to enable the wound margin and approximation to be adjusted in an incremental fashion, with the interlocking nature of the above mentioned nodes (not shown) with the eyelet 38 of each tissue anchor 10 negating the need to otherwise secure the suture to the anchors 10 by more conventional means. The shape and configuration of the tissue anchor 10 may also be varied in order to suit the particular surgical indication. For example the body of the tissue anchor may be defined as a curved surface which may be displaced between unfurled and furled states in order to effect displacement of sets of barbs between the un-deployed and deployed states described above.

FIGS. 15 to 31 illustrate a number of alternative embodiments of a tissue anchor according to the present invention. In each of these alternative embodiments like components have been accorded like reference numerals and unless otherwise stated perform a like function.

FIG. 15 illustrates a first alternative embodiment of a tissue anchor, generally indicated as 110. The anchor 1 to again comprises a first section 114 and a second section 116 reversibly displaceable relative to one another and is defined as being symmetrical, including an equal number of barbs on the first section 114 and the second section 116.

FIG. 16 illustrates a second alternative embodiment of a tissue anchor according to the present Invention, and generally indicated as 210. The anchor 210 comprises a first section 214 and a second section 216 displaceable relative to one another, the second section 218 having only a stogie barb projecting therefrom, defined as asymmetric.

FIGS. 17a to 17d illustrate various views of a third embodiment of a tissue anchor according to the present invention, generally indicate as 310. The tissue anchor 310 comprises a first section 314 and a second section 316 reversibly displaceable relative to one another. The first section 314 compromises an array of barbs 326 and the second section 318 also comprises an array of barbs 328. Unlike the first embodiment, the barbs 326 on the first section 314 extend substantially perpendicularly to the underside of the tissue anchor 310, while the barbs 328 on the second section 316 are inclined towards the barbs 326 of the first section 314.

FIGS. 18a to 18f illustrate various views of a fourth alternative embodiment of a tissue anchor according to the present invention, and generally indicated as 410. The tissue anchor 410 comprises a first section 414 between which is located a second section 418 which is displaceable relative to the first section 414, The first section 414 comprises an array of inclined barbs 426 while the second section 416 comprises a larger array of substantially perpendicularly extending barbs 428.

FIGS. 18a to 19d illustrate various views of a fifth alternative embodiment of a tissue anchor according to the present invention, generally indicated as 510. The tissue anchor 510 comprises a first section 514 and a second section 518 displaceable relative thereto, although in this embodiment the second section 516 is constrained for displacement along a two stage path by means of a number of keyways 524 provided on the first section 514, and within which a pair of guide rods 522 of the second section 516 are captured. FIG. 19b illustrates the tissue anchor 510 in the un-deployed state. FIG. 19c showing the tissue anchor 510 with the second section 516 partially displaced towards the deployed state and having completed the first stage of the relative displacement, while FIG. 19d Illustrates the tissue anchor 510 in the fully deployed state in which the second section 516 had traversed the second stage of the relative displacement defined by the keyways 524.

FIGS. 20a to 20e illustrate various views of a sixth alternative embodiment of a tissue anchor according to the present invention, generally indicated as 610 in this alternative embodiment the tissue anchor 810 is configured as a medical device, in particular a glucose monitor. The anchor 810 comprises a first section 614 which is composed of an inner and an outer disc-like component between which is captured a second section 618 which is in the form of an annular band located between the Inner and outer portions of the first section 814. The first section 814 and second section 616 are concentrically located and reversibly displaceable or rotatable relative to one another such as to effect the displacement of an array of barbs 626 on the first section 614 and a corresponding array of barbs 628 on the second section 616. The tissue anchor 610 additionally comprises a filament or probe 40 projecting from the underside of the anchor 610 and which, once foe anchor 610 is secured to a deployment site such as the skin of a patent, the probe 40 is inserted end remains within the skin or other tissue in order to perform the necessary medical function, such as for example monitoring blood sugar levels. It wifi of course be understood that any other form of probe or sensor may be alternatively or additionally provided on the tissue anchor 610.

FIGS. 21a to 21d illustrate various views of e seventh embodiment of a tissue anchor according to foe present invention and generally indicated as 710. A pair of the anchors 710 are linked or bridged together by means of a mount 46 which is adapted to receive and retain a cannula C therein, for example to hold an intravenous drip in position on the arm of a patient or the like such as a central venous fine, each of the anchors 710 being anchored in place on the skin of the patient as hereinbefore described.

FIGS. 22a to 22d illustrate various views of an eighth embodiment of a tissue anchor according to the present invention and generally indicated as 810, The tissue anchor 810 of this embodiment is designed to have a very low profile in order to suit particular applications, and comprises first and second sections 814, 816 which are sheet-like in form, and are preferably manufactured by punching and pressing the requisite forms from a sheet of material such as metal or the like. FIGS. 22a and 22c show the tissue anchor 810 in the undeployed state, FIG. 22c showing the anchor 810 lying on an upper surface of a tissue substrate in preparation for deployment, while FIGS. 22b and 22d show the anchor 810 in the deployed state, FIG. 22d illustrating the anchor 810 anchored to the tissue substrate. The anchor 810 comprises a tab 36a which is pressed partially out of the sheet forming the second section 816, while the first section 814 comprises a correspondingly shaped and located socket 36b which is punched entirely out of the material in order to receive the tab 836a therein in order to lock the first and second sections relative to one another in the deployed state or configuration.

FIGS. 23b to 23e illustrate various views of a ninth embodiment of a tissue anchor according to the present invention and generally indicated as 910. The tissue anchor 910 is similar in construction and configuration to the tissue anchor 810 of the previous embodiment, having first and second sections 814, 918 which are formed from flat sheet-like material to provide a low profile. The tissue anchor 910 is however designed to be displaced between a furled configuration as illustrated in FIG. 23a in which the longitudinal axis LL Is rectilinear, for example for introducing the anchor 910 to a site having restricted access, whether via the lumen of a medical device or the tike, and an unfurled configuration as illustrated in FIGS. 23b to 23e in which the longitudinal axis is curvilinear. The anchor 910 is thus formed having a curvature in the "Y" direction in order to retain the anchor 910 in the furled configuration, which wifi therefore require tire application of force in the "Z" direction in order to displace the anchor 910 into the unfurled configuration. FIGS. 23b and 23c show the anchor 910 in the unfurled and undeployed state while FIGS. 23d and 23e show the anchor 910 in tire unfurled and deployed state. In the unfurled configuration the anchor 910 is curved in the "X" direction, along the longitudinal axis LL, and is intended for use in applications in which the surface of the tissue to which the anchor 910 is to be secured has a similar curvature, for example a wall of the bowel or the like. The various openings or fenestrations in first and second sections 914, 916 of the anchor 910 provide increased flexibility to the anchor 910 in order to facilitate displacement between the furled and unfurled configurations. It will of course be appreciated that this functionality may be achieved in any number of alternative ways.

FIGS. 24a to 24d illustrate various views of a tissue anchor according to a tenth embodiment of the present invention, and generally indicated as 1010. The anchor 1010 of this embodiment is very similar is design and construction to the anchor 810 of the eighth embodiment, but includes a curvature or concave aspect in the "Y" direction, again preferably to better conform to a curved tissue surface white having a very low profile. First and second sections 1014, 1016 of the anchor 1010 are again preferably formed from a sheet-tike material and most preferably are stamped or otherwise formed from sheet metal or the like. Barbs 1026, 1028 can then simply be bent outwardly in the "Z" direction in order to provide the opposing arrays operable to achieve shear deformation of the tissue when displaced from the undeployed into the deployed state in order to effect retention of the anchor 1010 on said tissue.

FIGS. 25a to 25d illustrate an eleventh embodiment of a tissue anchor according to the present invention, and generally indicated as 1110. This eleventh embodiment is effectively a further alternative in which the anchor 1110 is displaceable between a furled configuration as illustrated in FIGS. 25a to 25c and an unfurled configuration as illustrated in FIG. 25d. In the furled configuration the anchor 1110 is rolled into a cylindrical form which makes it suitable to be deployed through the lumen of a delivery device such as a catheter (not shown) or the like, and once located at a deployment site the anchor 1110 is displaced into the unfurled configuration in which the tubular furled arrangement opens outwardly into a flat sheet in preparation for displacement from the undeployed to the deployed stale. The anchor 1110 may then be displaced from the undeployed configuration shown in FIG. 25d into the deployed configuration by displacing first and second sections 1114, 1116 relative to one another in order to embed barbs 1126, 1128 into the tissue in order to achieve anchorage.

FIGS. 26a to 26d illustrate a twelfth embodiment of a tissue anchor according to the present invention, and generally indicated as 1210. The anchor 1210 defines a much greater surface area on which opposing array of barbs 1226, 1228 are arranged, end is intended to be used as e support on which a layer of real or artificial tissue (not shown) can be retained in order to act as a test substrate for various uses, for example testing of one or more of the tissue anchors of the previous embodiments. First and second sections 1214, 1216 of the anchor 1210 comprise multiple interlocking portions and as with ell previous embodiments are displaceable relative to one another in a first direction parallel to a longitudinal axis t-L of the anchor 1210 in order to displace the anchor 1210 between the undeployed state shown in FIGS. 25a, 26c and 25d and the deployed state as illustrated in FIG. 25b. In use a layer of tissue is laid over the array of barbs 1226, 1228 with the anchor 1210 in the undeployed configuration, and the first and second sections 1226, 1228 are then displaced relative to one another in order to move the anchor 1210 into the deployed state. This draws the barbs 1226, 1228 into the tissue thereby effecting robust retention of the layer of tissue on the anchor 1210. This tissue can then be used as a test substrate as hereinbefore described, the tissue anchor 1210 providing a robust and rigid backing or platform to the tissue substrate in order to allow testing to be carried out thereon, as detailed hereinafter.

Figure 28A:
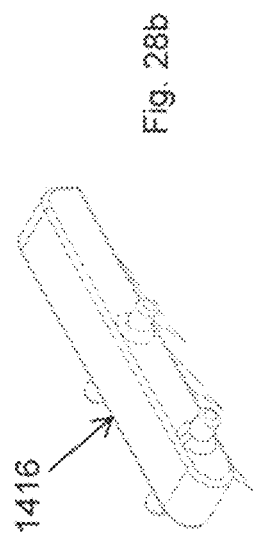
Figure 28B:
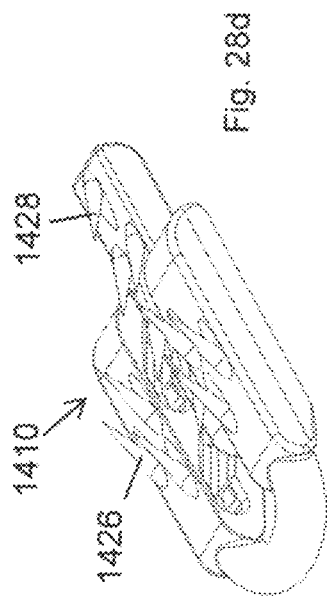
Figure 28D:
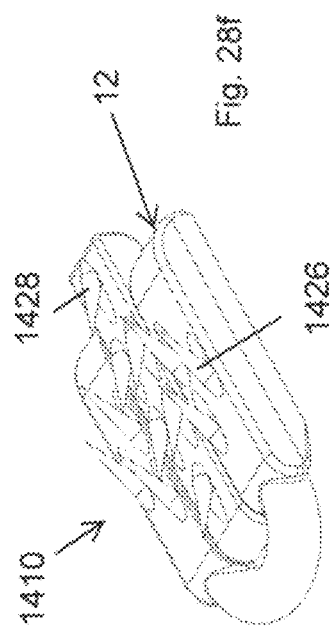
Figure 28C:
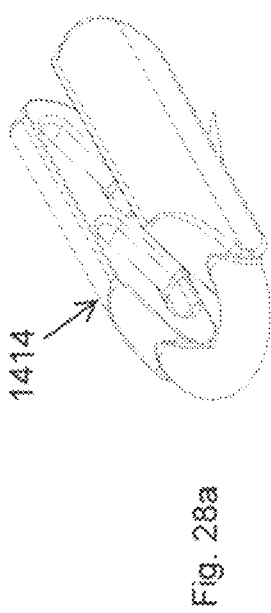
Figure 28E:
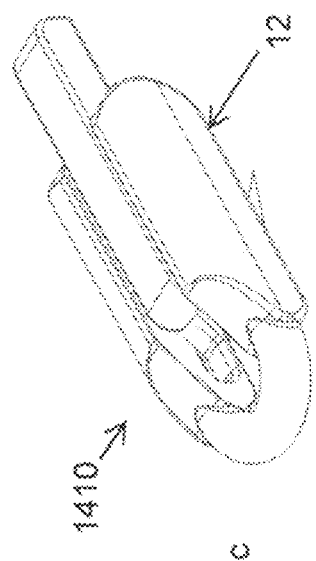
Figure 28F:
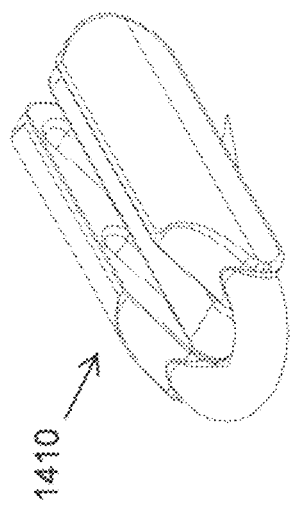

FIGS. 27a to 27d illustrate a thirteenth embodiment of a tissue anchor according to the present invention, and generally indicate as 1310. This thirteenth embodiment is essentially identical to the twelfth embodiment other than the provision of a region devoid of barbs 1326, 1328 which in use can allow one or more medical or surgical devices to be passed directly through a layer of tissue secured to the anchor 1310, in order to simulate a particular surgical or medical scenario for testing purposes. FIGS. 28a to 28i illustrate various views of a fourteenth embodiment of a (issue anchor according to the present invention, generally indicated as 1410. The tissue anchor 1410 comprises a body 1412 comprising a first section 1414 and a second section 1416 engagable with and relative to the first section 1414 between an undeployed state as illustrated in FIGS. 28c, 28d and 28g, and a deployed state as illustrated in FIGS. 28e, 28f and 28i. The first section 1414 is illustrated in isolation in FIG. 28a while the second section 1416 is illustrated in isolation FIG. 28b. In the undeployed state barbs 1428 on the first section 1414 are disposed at a different height in the "Z" direction relative to barbs 1428 on the second section 1416. Deployment from the undeployed to the deployed state both displaces the barbs 1426, 1428 towards one another in the "X" direction and into alignment in the "Z" direction.

FIGS. 29a to 29d illustrate various use of the fifteenth embodiment of a tissue anchor according to the present invention, and generally indicated as 1510. The anchor 1510 comprises a body 1512 having a first section 1514 having barbs 1526 arranged in a circular array and pointing radially inwardly, and a second section 1516 again having barbs 1528 arranged in a circular array concentrically of the barbs 1526, but feeing radially outwardly towards the barbs 1526. In the particular embodiment illustrated the first section 1514 remains stationary while the second section 1516 is displaced radially outwardly in order to effect displacement of the anchor 1510 from the undeployed configuration as illustrated in FIGS. 29a and 29c into the deployed state as illustrated in FIGS. 29b and 29d. It will however be understood that the anchor 1510 may be arranged such that both the first and second sections 1514, 1516 undergo displacement as the anchor 1510 is displaced between the undeployed and deployed states.

FIGS. 30a to 30d illustrate a sixteenth embodiment of a tissue anchor according to the present invention, and generally indicated as 1610. In this embodiment a number of the barbs 1628 have a particular directional bias m the form of an angular inclination in the "Y" direction in order to improve anchoring. More particularly this directional bias serves to increase resistance to withdrawal of the barbs 1626 from tissue into which they are secured in applications such as that shown in FIGS. 11 and 12 where a transverse force is applied to the deployed anchor 1610, acting above the surface of the tissue in which the anchor is secured, thereby effectively generating a rotational force or torque which acts to draw the barbs 1626, 1628 out of the tissue. For comparative purposes FIG. 30a shows the anchor 1610 with no angular offset or directional bias to the barbs 1626, which will therefore provide no improvement in resistance to the above described torque, which would be applied via an eyelet 1638 on the anchor 1610 for securing a suture or the like. FIG. 30b illustrates the anchor 1810 in which the barbs 1626 of the first section 1814 are aligned such that the tip of the barbs 1626 are rotated outwardly and away from the barbs 1628 of the second section 1618. FIG. 30c illustrates the anchor 1810 with the barbs 1626 all rotated towards the side of the anchor 1610 on which the eyelet 1638 is positioned. FIG. 30d illustrates the anchor 1810 with all of the barbs 1628 rotated inwardly towards the barbs 162B. The improvements gained from various directional biases of the barbs 1626 are shown in FIG. 34b as detailed hereinafter. Equally, the barbs 1628 of the second section 1616 could also exhibit rotational bias.

FIGS. 31a to 31d illustrate a seventeenth embodiment of a tissue anchor according to the present invention, and generally indicated as 1710. In this embodiment the anchor 1710 comprises a body 1712 comprising a first section 1714 and a second section 1718 displaceable relative to one another between an undeployed state illustrated in FIGS. 31a and 31c and a deployed state as illustrated in FIGS. 31b and 31d. The anchor 1710 operates essentially in reverse to that of the previous embodiments: in that barbs 1726, 1728 of the first and second section 1714, 1716 are overlapping in the "Y" direction when in the undeployed state, with displacement into the deployed state moving the sets of barbs 1726, 1728 away from one another. However, as the barbs 1726, 1728 overlap in the undeployed state, displacement into the deployed still has the effect of applying the same shear deformation to the tissue surrounding or acted on by the barbs 1726, 1728, in order to achieve robust retention in the tissue as hereinbefore described with reference to the previous embodiments.

Figure 38A:
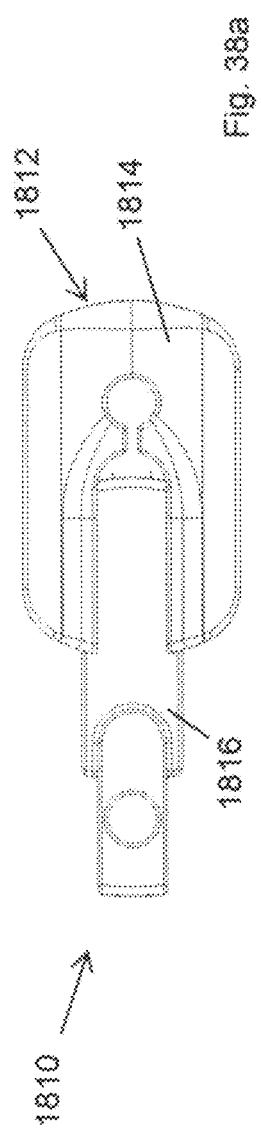
FIGS. 38a to 38d illustrate various views of a seventeenth alternative embodiment of a tissue anchor according to the present invention.
Figure 38B:
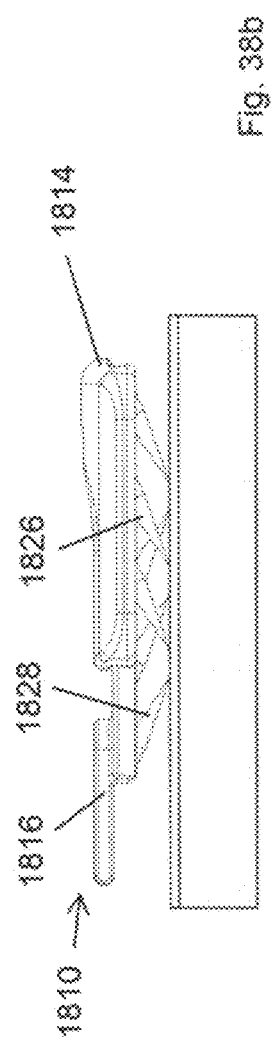
Figure 38C:
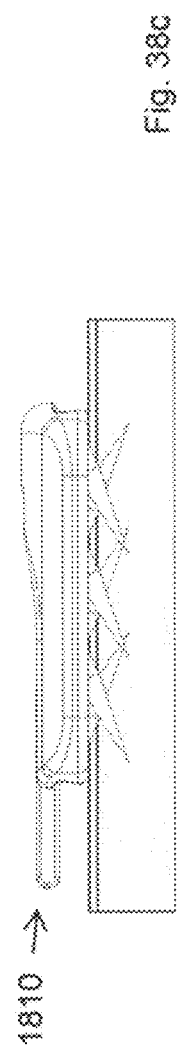
Figure 38D:
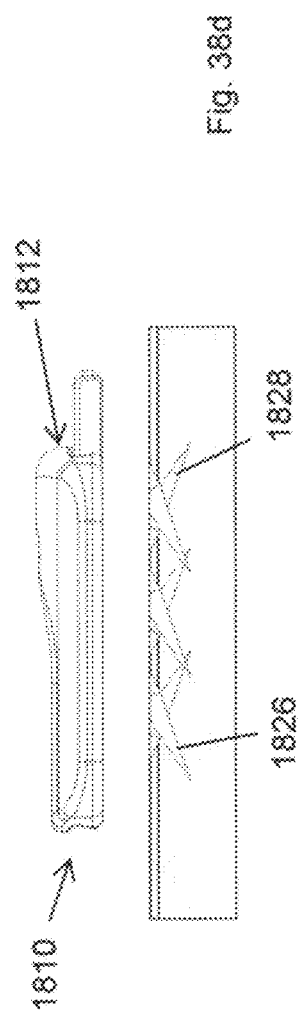

FIGS. 38a to 38d illustrate an eighteenth embodiment of a tissue anchor according to the present invention, and generally indicated as 1810, which is particularly intended for use in drug delivery via microneedles 1828, 1828 provided on first and second sections 1814, 1818 respectively of a body 1812 of the anchor 1810. The anchor 1810 is designed to be anchored to a tissue substrate, for example the skin, in predominantly the same manner as hereinbefore described with reference to the previous embodiments. Thus the microneedles 1826, 1828 are embedded into the tissue through displacement of the anchor 1810 from the undeployed state as illustrated in FIGS. 38a and 38b to the deployed state as illustrated in FIG. 38c, At feast some and preferably at of the microneedles 1826, 1828 comprise resorbable drug eluting microneedles, and the anchor 1810 is therefore designed to allow the microneedles 1826, 1828 to be sheared off the body 1812 so as to be left embedded in the tissue to effect drug delivery over a period of time before being absorbed into the tissue. The method of deployment thus involves additional displacement of the first and second sections 1814, 1816 relative to one another, beyond that required to embed the microneedles 1826, 1828, which additional displacement serves to shear off the microneedles 1828, 1828 from the body 1812 as illustrated in FIG. 38d.

Each of the microneedles 1826, 1828 may therefore be provided with a designed point of weakness to facilitate this shear failure in order to avoid undue shear deformation of the surrounding tissue during the additional displacement of the sections 1814, 1816. The shearing of the microneedles 1826, 1828 could equally be achieved using an other suitable alternative mechanism (not shown) designed into the anchor 1810.

EXAMPLES OF EXPERIMENTAL RESULTS

Prototypes of a number of the above described embodiments of the tissue anchor of the invention were produced to both test the manufacturability of the anchor in addition to testing the efficacy of the tissue anchor in various surgical and medical indications, the results of which are set out hereinafter.

Example 1—Microneedle-Based Anchor Fabrication

There are many suitable methods for producing the microstructure and microneedle arrays utilised in the tissue anchors according to the various embodiments of the present invention, including micro-moulding and replica moulding techniques. In this example the microneedle-based tissue anchors were produced from surgical grade 316L stainless-steel using a 30 printing technique that is commonly used (ConceptLaser GmBH, Germany), and can easily be reproduced Two embodiments of the present invention were produced for subsequent testing, and which were optimised for different intended clinical applications. In embodiment A, the design height ($L_z$) of the microneedle tips from the substrate, and the maximum perpendicular depth of penetration into the skin was limited to 1000 μm. In embodiment B, the design height ($L_z$) of the microneedle tips from the substrate was limited to 750 μm. Appreciably, any layered deposition 30 rapid-prototyping manufacturing technique (metallic or polymeric) imposes several limitations on the geometry of the microneedle features, including a limit to the resulting resolution or sharpness of the microneedle tips. An average microneedle tip radius on the produced parts of approximately 20 μm was estimated using optical imaging and analysis techniques. Accordingly, the resulting height of the rounded microneedle tips from the substrate was approximately 900 μm and 690 μm for Embodiment A and Embodiment B, respectively.

Embodiment A and B exhibited 12 microneedles m total and which were oriented at 26.5° from the substrate. The length (L) and base diameter of the microneedles for Embodiment A and B was 2.24 mm and 600 μm, and 1.68 mm and 450 μm, respectively. The x-spacing and y-spacing of the microneedles was set to 2.5 mm and 1 mm, respectively, whilst the lateral spacing between the inner and outer rows of sliding microneedles was set at 1.5 mm. Shear deformation was applied to the tissue in this zone by employing a translational overlap of 1 mm and 0.75 mm for Embodiment A and Embodiment B, respectively, corresponding to 50% of the x-component of the microneedle length ($L_x$).

To facilitate in vitro biomechanical testing of the microneedle-based tissue anchors in porcine skin a variant of the tissue anchor according to the present invention in the form of a tissue bed was developed as a means of securing the skin samples to the testing machine and based on the embodiment described with reference to FIGS. 26a to 26e. Tissue beds and anchor parts utilised in Example 2 and Example 3 testing were prepared using a polymer rapid prototyping technique (Form2, Formlabs). Resulting radii of the microneedle tips was estimated to be 15 μm using said optical imaging and analysis techniques. Porcine skin was the chosen in vitro test medium as it has been shown to have similar histological, physiological and biomechanical properties to human skin and has been suggested as a good analogue for medical research.

Example 2—In Vitro Mechanical Testing of Devices in Synthetic Skin

The effect of directional biasing of the barbs was investigated in a synthetic skin analogue (Syndaver labs, FL, USA), as shown in the FIG. 32. The method of testing was as described in Example 3. FIG. 32 shows the mean maximum force that each anchor was able to resist before being forcibly withdrawn from the tissue. It is clear that the anchor shown on the right, having directional biasing of the barbs towards the eyelet, exhibit the greatest resistance to withdrawal.

Example 3—In Vitro Mechanical Testing of Devices in Porcine Skin

In the following study, a preliminary analysis was performed to quantify the in vitro mechanical anchorage strength of Embodiments A and 8 attached to porcine skin in a direction transverse to the alignment of the microneedles as well perpendicular to skin. The test devices were attached to porcine skin harvested from minipigs sacrificed for unrelated experiments. Tissue was immediately wrapped in saline-soaked gauze and frozen on the day of harvest and defrosted on the day of testing. Tissue samples were mechanically secured to a tissue testing platform described in Example A and FIGS. 26 and 33, and attached to the lower mount of an electromechanical testing machine (Hounsfield, Tinius Olsen) as shown to FIG. 35. Embodiments A and B were deployed on the skin and attached to a 1 kN load ceil secured to the crosshead of the testing machine via a length of braided polyester suture (#2 Ethibond, Ethicon). Samples were destructively tested at a displacement rate of 10 mm·min$^{-1}$ and force-displacement date recorded continuously. A gauge length of 50 mm was maintained for all tests. N=6 microneedle anchors of each type were tested in each orientation, and the results are shown in FIG. 33.

The results indicate that the microneedle-based devices (Embodiments A and B) are able to efficiently grip porcine skin, indicating that such a device will be able to serve as mechanics) anchors for use in skin, as well as other soft and hard biological tissues. Component parts (first section 14 and second section 16) of Embodiment A were also individually tested in the transverse and perpendicular orientations, yielding ultimate force values of 14.7±0.5N (section 14) and 5.7±2N (section 16), respectively, implying a positive synergistic effect when sections 14 and 16 are engaged in the tissue according to the present invention.

Example 4—Ex Vivo Histological Assessment of Insertion into Porcine Skin

The following study was conducted to assess the depth of penetration of the microneedles of Embodiment A into fresh-frozen porcine tissue. As a control, standard microneedle arrays (MNA's) were developed and printed in 316L stainless steel using a 3D metal printer (Concept Laser GmbH, Germany). These control MNA device consisted of a 5×5 matrix of microneedles exhibiting identical length and base diameter dimensions as the individual microneedles of Embodiment A (test group). The length L and base diameter of the microneedles were set to 2.24 mm and 600 μm, respectively, with equal x- and y-spacing of 1.5 mm.

The test devices were attached to porcine skin harvested from minipigs sacrificed for unrelated experiments. Tissue was immediately wrapped in saline-soaked gauze, frozen and defrosted on the day of testing. Embodiment A devices were attached using hand-held parallel-jawed pliers. MNA's were deployed onto the skin by applying a normal force to underside of the base using a hand-held force gauge (Sauter, Germany) using three different force levels: 12.5N, 25N and 50N. The tissue samples with test devices in situ were immediately fixed in 10% phosphate buttered formalin (Sigma-Aldrich) for subsequent histological processing. After 48 hours of fixation, the test devices were manually removed from the tissue and tissue blocks prepared for paraffin embedding. A microtome was used to translate through the full-depth of each paraffin-embedded block in 6 μm-thick sections in a plane perpendicular to the skin surface, coincident with the microneedle axis. Slides were then stained with haematoxylin and Eosin (H&E) using an automated slide stainer (Leica) and imaged using a transmitted light microscope (Leica). A minimum of 40 individual sections were obtained coincident with each row of microneedles, encompassing each microneedle tip.

Figure 34:
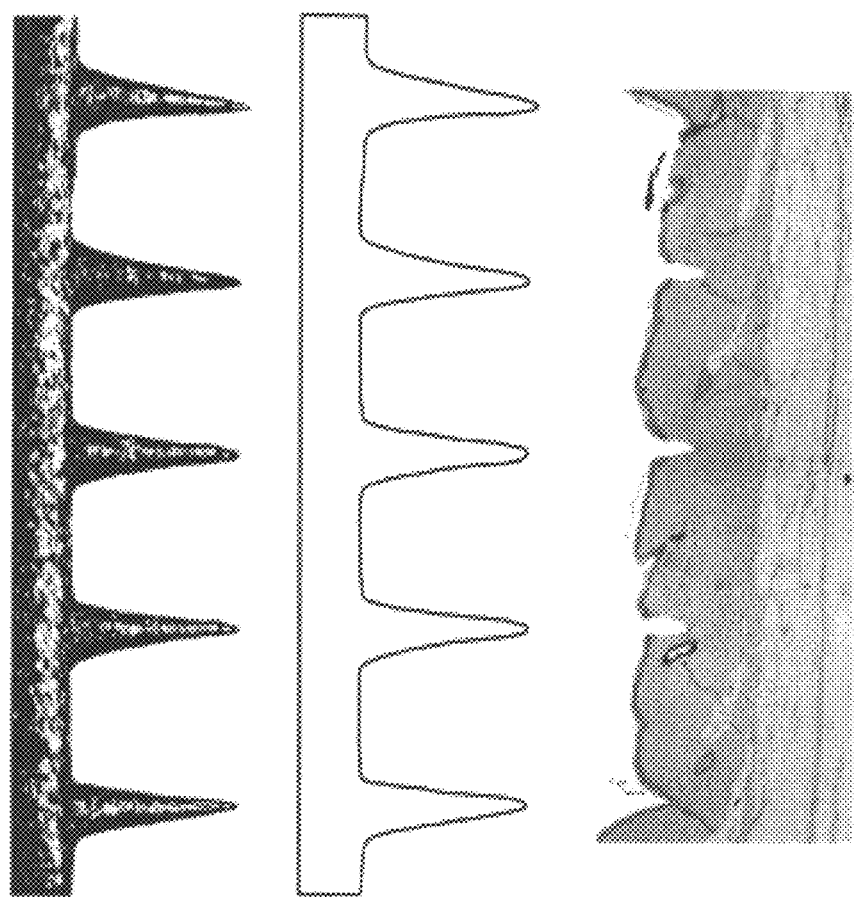
FIG. 34 illustrates a macroscopic overview of a microneedle array sample (top), a corresponding outline (middle) and histological image showing the depth of penetration of the microneedles, for comparison purposes with microneedles found on a tissue anchor according to the invention.
Figure 35:
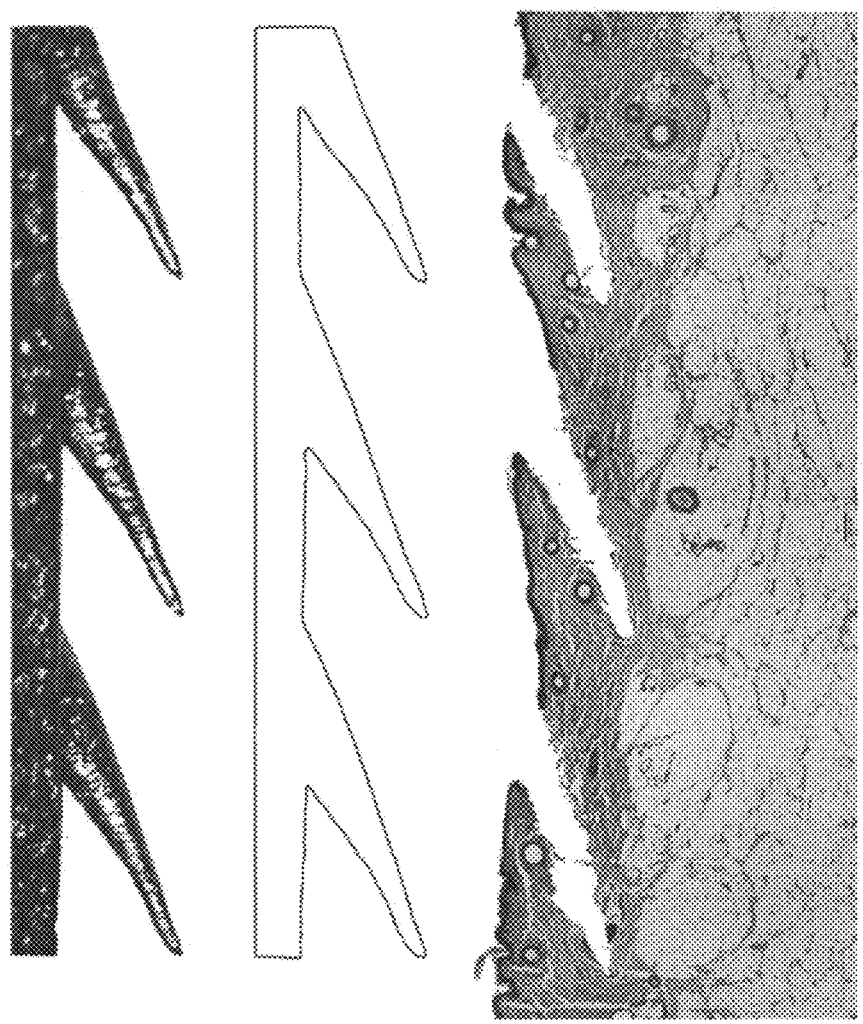
FIG. 35 illustrates an overview of a microneedle array as configured for use on a tissue anchor according to the present invention (top), a corresponding outline (middle) and histological image showing the depth of penetration of the microneedles.

Serial images were imported into Imaged (NiH), scaling applied and tee vertical depth of penetration of the needles into the tissue measured, as shown in FIGS. 34 and 35. A minimum of 40 sections about each microneedle tip were analysed to ensure that the maximum depth of tissue penetration (corresponding to the microneedle tip) was captured.

Results

The MNA samples implanted with 12.5N of force (average of 0.5N per microneedle in the 5×5 array) did not remain in situ during fixation, and histological examination did not reveal microneedle penetration, suggesting that this force level was insufficient to produce needle insertion. Results for the remaining test groups and conditions are shown in FIG. 38.

Figure 36:
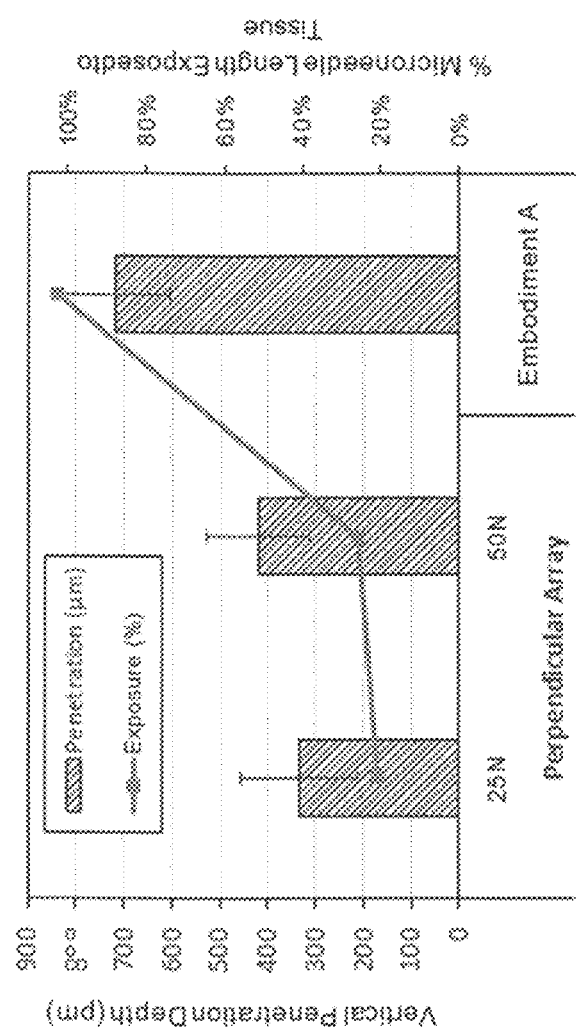
FIG. 36 illustrates histological results of tests carried out on an embodiment of a tissue anchor according to the present Invention.

The results demonstrate that Embodiment A is more effective at penetrating skin than the MNA's at two different levels of force which would be appropriate for a rigid 5×5 array of microneedles as used in vaccine and drug-delivery applications. The histological results for Embodiment A shown in FIG. 36 revealed that approximately 103% of the leading edge was exposed to tissue, suggesting that the recesses present at the base of each microneedle capture an amount of displaced tissue during implantation. The histological results of Embodiment A samples consistently revealed an intact stratum corneum behind the non-leading edge, implying that the traction applied to tee skin by relative motion of the opposing rows of microneedles promotes immediate mechanical anchorage and lack of relative slippage of the microneedle tips along the skin during the initial stage of deployment.

Example 5—Wound Closure Application in an Ex-Vivo Porcine Model

The fallowing example outlines a preliminary ex vivo animal study that was performed to assess the wound closing efficiency of the micro needle-based anchors in the closure of elective wounds. Embodiment A versions of the tissue anchor were applied to the dorsal aspect of minipigs sacrificed for an unrelated experiment. Eight tissue anchors were disposed symmetrically about a line at a spacing of approximately 22-24 mm. An incision was then made to simulate a surgical wound. The deeper layers were then closed with a running suture, followed by closure of the superficial skin by lacing suture through the open eyelets of the individual tissue anchors.

Results

The result demonstrates that the microneedle-based tissue anchors offer a less-invasive means to rapidly and robustly reduce planned incisions in a clinical setting, producing eversion of the skin edges which promotes healing.

Example 6—Preliminary Human Study

The following example outlines a preliminary human study that was performed to assess the in vivo performance of Embodiment 8 in a human volunteer. The aims of the study were as follows:

To assess whether application of the device induces pain
To monitor inflammatory responses induced by the devices
To test adherence of the devices
To assess whether removal of the device induces pain 3D-printed 316L stainless steel versions of Embodiment 8 were electropolished, sonicated in isopropyl alcohol, lavaged in distilled water and steam-sterilised in an autoclave. The skin over the deltoid tuberosity of the humerus (upper arm) was shaved and non-viable cells and oils removed using an alcohol wipe. Antiseptic cream (Bepanthen) was applied to the area and allowed to dry. Five tissue anchors were applied to the skin in a fine extending proximal to distal, during which the volunteer was asked to assess the pain associated with insertion of each of the devices on a visual analogue scale from 0-10. The devices were left uncovered and the volunteer given care instructions for the attachment site.

To assess the initial skin response to application and immediate removal of Embodiment A of the microneedle-based tissue anchor the device in position 1 was removed after approximately 10 minutes (time 0 site). The tissue response to prolonged wearing of the device was assessed after 3, 5, 7 and 9 days by removing a single device at each of these timepoints. Discomfort/pain, inflammatory responses and the stability of the device placement was observed daily for the 9 days that the devices were worn by the volunteer and daily thereafter, for up to 32 days after initial device placement. The application site was not protected with medical bandaging or similar.

Results

The volunteer reported mild pain upon application of the devices (approximately 1-2 on a visual analogue scale of 0 to 10). Pain disappeared within 16 minutes of application and then the devices were painless for the duration of their application to the skin (which ranged from 3-9 days). Observations were made on a daily basis, and all devices appeared to be firmly and rigidly attached to the skin for the entire period of application, and no infections or adverse effects were observed. For Embodiment B, erythema appeared in the skin after placement of the device at time 0. Small puncture wounds corresponding to the microneedles were observed, but which did not produce bleeding. Embodiment B versions of the device remained on the skin for a range of 3-9 days. When the devices were removed on days 3, 5, 7 and 9 swelling (edema) was observed in addition to erythema. The volunteer reported minimal-to-no pain (0-1 on a VAS of 9-10) during removal of tire devices on days 3, 5, 7 and 9. In an cases, the normal appearance of the skin had returned after approximately 2-4 weeks.

Summary

In summary, the results of the present study showed that the devices can be applied to the skin with little pain and can remain firmly attached to the skin for several days. This and other data strongly support that the present microneedle based devices represent an attractive alternative to conventional methods of anchoring to human skin.

Example 7—Electromyography (EMC) Measurement in a Human Volunteer

The following example outlines a preliminary human study that was performed to demonstrate functionality of Embodiment B of the microneedle anchor when used as an elect rode for EMG measurement during an isometric contraction of the biceps brachii muscle. Specifically, the aims of the study were to (1) determine whether Embodiment B could reproduce the EMG signal measured by a standard wet electrode, and (2) determine the strength (Vrms) and signal-to-noise ratio (SNR) mid-contraction of the two electrodes.

Figure 37:
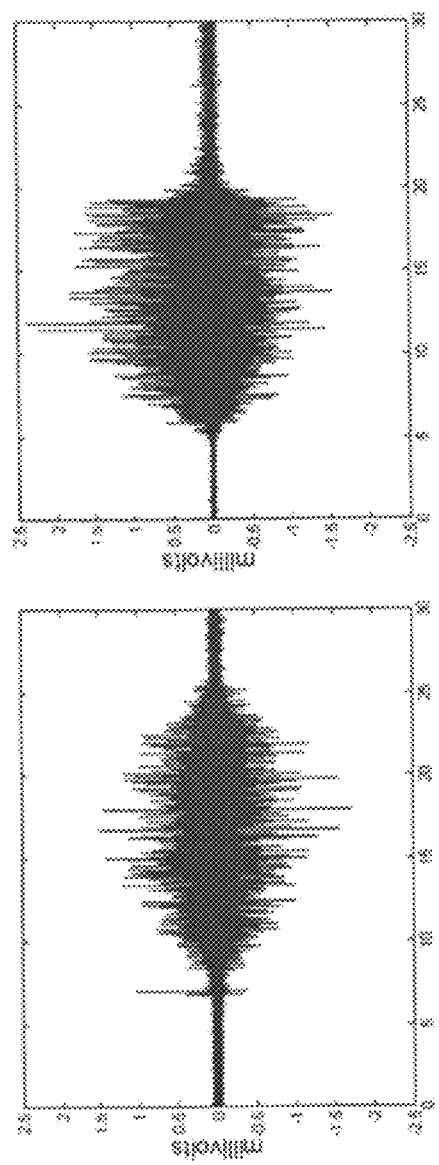
FIG. 37 illustrates GMG data from wet electrodes (left) and an electrode as defined by a tissue anchor according to an embodiment of the present invention (right)

Measurements were made using bipolar pairs of standard wet Ag/AgCl and embodiment 8 electrodes as shown respectively on the left and right hand sides of FIG. 42*a*. Prior to recording a standard skin preparation technique involving fight sanding of the site and cleansing with an alcohol wipe to remove non-viable cells and oils from the surface was performed on the dominant arm. During the experiment the subject maintained their elbow in 90° of flexion unloaded and whilst supporting an 8.5 kg weight. Results from the experiment are shown on the left and right hand sides of FIG. 37.

Results

EMG data for each device applied to the same subject during a 2-second window mid-contraction were analysed and normalised to the basal (relaxed) state, generating Vrms and SNR ratios of 0.2698 mV and 20 90871 dB, 0.3274 mV and 30.04483 dB for the standard wet and Embodiment 8 electrodes, respectively. This data demonstrates that Embodiment 8 can be used reliably to measure EMG signals.

The invention claimed is:

1. A tissue anchor comprising a body having a first section and a second section displaceable in a first "X" direction relative to one another to translate the tissue anchor between an undeployed state and a deployed state; at least one first protrusion projecting from the first section and at least one second protrusion projecting from the second section, one of the at least one first protrusion and the at least one second protrusion being inclined towards the other of the at least one first protrusion and the at least one second protrusion; and wherein the at least one first protrusion on the first section and the at least one second protrusion of the second section overlap in the first "X" direction and a second "Z" direction substantially A perpendicular to the first "X" direction when the anchor is in the undeployed and deployed state.

2. A tissue anchor according to claim 1 in which each protrusion comprises a root and a tip, each protrusion being aligned from the root to the tip in a direction substantially parallel to the first direction.

3. A tissue anchor according to claim 1 in which each protrusion comprises a barb.

4. A tissue anchor according to claim 1 in which the first section and the second section each comprise a plurality of protrusions.

5. A tissue anchor according to claim 4 in which the first section and the second section comprise equal numbers of the plurality of protrusions.

6. A tissue anchor according to claim 4 in which the plurality of protrusions on both the first and second sections are arranged in a rectangular array.

7. A tissue anchor according to claim 4 in which the plurality of protrusions on the first and the second section are arranged in concentric circular arrays.

8. A tissue anchor according to claim 1 in which the plurality of protrusions comprise micro features.

9. A tissue anchor according to claim 1 in which the first section and the second section each define a tissue contacting surface from which the respective at least one first protrusion and/or the at least one second protrusion extend respectively.

10. A tissue anchor according to claim 9 in which the tissue contacting surface of the first section and/or the second section comprises a recess located at or adjacent a root of the first protrusion and/or the at least one second protrusion respectively.

11. A tissue anchor according to claim 1 in which the first section comprises a first set of the at least one first protrusions and a second set of the at least one protrusions spaced from the first set of at least one first protrusions, the second section being displaceable relative to the first section along a path between the first and second set of the first protrusions of the first section.

12. A tissue anchor according to claim 1 in which one or more of the first protrusions on the first section extends obliquely with respect to the first "X" direction.

13. A tissue anchor according to claim 1 comprising a lock operable to fix the first and second sections relative to one another.

14. A tissue anchor according to claim 1 in which the first section defines a channel adapted to at least partially receive the second section therein.

15. A tissue anchor according to claim 14 in which the channel is open at one end.

16. A tissue anchor according to claim 1 comprising at least one micro-needle.

17. A tissue anchor according to claim 16 in which at least one of the at least one first protrusion and the at least one second protrusions comprises a micro-needle.

18. A wound closure system comprising an array of the tissue anchors according to claim 1; and at least one tensile member tethered between at least two of the tissue anchors.

19. A method of securing a tissue anchor to tissue, the method comprising the steps of inserting at least one first protrusion projecting from a first section of a body of the anchor and at least one second protrusion projecting from a second section of the body into the tissue; displacing in a first "X" direction the first section relative to the second section to translate the tissue anchor from an undeployed state to a deployed state, wherein the at least one first protrusion on the first section and the at least one second protrusion on the second section overlap in the first "X" direction and a second "Z" direction substantially perpendicular to the first "X" direction when the body is in the undeployed and deployed state; such as to effect localised deformation of the tissue surrounding the at least one first protrusion and the at least one second protrusions when the body is in the deployed state.

20. A method according to claim 19 in which the step of displacing the first section relative to the second section is effected in two stages, a first stage in which the relative displacement primarily effects insertion of the at least one first protrusion and the at least one second protrusions into the tissue, and a second stage which primarily effects the localised deformation of the tissue surrounding the protrusions.

\* \* \* \* \*

UNITED STATES PATENT AND TRADEMARK OFFICE
CERTIFICATE OF CORRECTION

PATENT NO. : 11,298,124 B2
APPLICATION NO. : 16/341199
DATED : April 12, 2022
INVENTOR(S) : Nicky Bertollo et al.

It is certified that error appears in the above-identified patent and that said Letters Patent is hereby corrected as shown below:

In the Specification
Column 1, Line 6: "including akin" should read --including skin--
Column 1, Line 7: "arterial well" should read --arterial wall--
Column 1, Line 9: "include bid" should read --include but--
Column 1, Line 32: "potential" should read --potentially--
Column 2, Line 19: "substantial" should read --substantially--
Column 2, Line 23: "find section" should read --first section--
Column 2, Line 33: "fee first" should read --the first--
Column 2, Line 38: "fee first" should read --the first--
Column 2, Line 41: "fee protrustions on fee first" should read --the protrusions on the first--
Column 2, Line 46: "fee second" should read --the second--
Column 2, Line 47: "fee channel" should read --the channel--
Column 2, Line 55: "fee protrusions" should read --the protrusions--
Column 3, Line 7: "fire invention" should read --the invention--
Column 3, Line 16: "rotative to" should read --relative to--
Column 3, Line 17: "fire present" should read --the present--
Column 3, Line 20: "body of fire" should read --body of the--
Column 3, Line 24: "fire tissue" should read --the tissue--
Column 3, Line 25: "protrusion on fee" should read --protrusion on the--
Column 3, Line 27: "substantiality perpendicular" should read --substantially perpendicular--
Column 3, Line 34: "locking me" should read --locking the--
Column 3, Line 35: "me second" should read --the second--
Column 3, Line 40: "end a" should read --and a--
Column 3, Line 67: "fire accompanying" should read --the accompanying--
Column 4, Line 54: "FIG. 18" should read --FIG. 16--
Column 4, Line 62: "FIGS. 19a to 18d" should read --FIGS. 19a to 19d--
Column 5, Line 16: "FIGS. 26a to 28d" should read --FIGS. 26a to 26d--
Column 5, Line 55: "GMG data" should read --EMG data--
Column 6, Line 3: "bowel wait" should read --bowel wall--
Column 6, Line 15: "(issue anchor" should read --tissue anchor--

Signed and Sealed this
Thirty-first Day of May, 2022

*Katherine Kelly Vidal*

Katherine Kelly Vidal
*Director of the United States Patent and Trademark Office*

CERTIFICATE OF CORRECTION (continued)  Page 2 of 4
U.S. Pat. No. 11,298,124 B2

Column 6, Line 34: "section 15" should read --section 16--
Column 6, Line 36: "deployed slate" should read --deployed state--
Column 6, Line 49: "white the side" should read --while the side--
Column 6, Line 51: "It wifi" should read --it will--
Column 7, Line 5: "folly into" should read --fully into--
Column 7, Line 10: "lip 34" should read --tip 34--
Column 7, Line 28: "trial all" should read --that all--
Column 7, Line 30: "to sun different" should read --to suit different--
Column 7, Line 42: "barbs 26" should read --barbs 28--
Column 7, Line 54: "adjacent herbs" should read --adjacent barbs--
Column 7, Line 55: "L sub y" should read --L sub x--
Column 7, Line 56: "barbs 28" should read --barbs 26--
Column 8, Line 12: "rotative displacement" should read --relative displacement--
Column 8, Line 16: "folly deployed" should read --fully deployed--
Column 8, Line 52: "white the" should read --while the--
Column 8, Line 61: "section 18" should read --section 16--
Column 8, Line 64: "section 18" should read --section 16--
Column 9, Line 2: "socket 38b" should read --socket 36b--
Column 9, Line 7: "when replacing" should read --when displacing--
Column 9, Line 16: "socket 38b" should read --socket 36b--
Column 9, Line 28: "relatively email" should read --relatively small--
Column 9, Line 42: "to order" should read --in order--
Column 9, Line 61: "Wood vessels" should read --blood vessels--
Column 9, Line 62: "advantageous to" should read --advantageous in--
Column 10, Line 5: "system, it is also" should read --system. It is also--
Column 10, Line 7: "whereto the barb" should read --wherein the barb--
Column 10, Line 16: "toe barbs" should read --the barbs--
Column 10, Line 30: "compose at least" should read --comprise at least--
Column 10, Line 59: "fast section" should read --first section--
Column 10, Line 66: "foil array" should read --full array--
Column 10, Line 67: "sutures" should read --suture S--
Column 11, Line 2: "foe suture" should read --the suture--
Column 11, Line 13: "me array" should read --the array--
Column 11, Line 14: "template 80" should read --template 60--
Column 11, Line 21: "once aft" should read --once all--
Column 11, Line 39: "anchors 10 wifi" should read --anchors 10 will--
Column 11, Line 48: "FIGS. 9-12, in use" should read --FIGS. 9-12. In use--
Column 12, Lines 6-7: "Knot like nodes" should read --knot like nodes--
Column 12, Lines 26-27: "anchor 1 to again" should read --anchor 110 again--
Column 12, Line 35: "section 218 having only a stogie" should read --section 216 having only a single--
Column 12, Line 43: "section 318" should read --section 316--
Column 12, Line 53: "section 418" should read --section 416--
Column 12, Line 58: "FIGS. 16a to 19d" should read --FIGS. 19a to 19d--
Column 12, Line 62: "section 518" should read --section 516--
Column 13, Line 10: "as 610 in this" should read --as 610. In this--

CERTIFICATE OF CORRECTION (continued)
U.S. Pat. No. 11,298,124 B2

Column 13, Line 11: "tissue anchor 810" should read --tissue anchor 610--
Column 13, Line 12-13: "anchor 810" should read --anchor 610--
Column 13, Line 15: "section 618" should read --section 616--
Column 13, Line 17: "first section 814. The first section 814" should read --first section 614. The first section 614--
Column 13, Line 24: "foe anchor" should read --the anchor--
Column 13, Line 25: "skin of a patent" should read --skin of a patient--
Column 13, Line 25: "inserted end" should read --inserted and--
Column 13, Line 28: "It wifi" should read --It will--
Column 13, Line 31: "of e seventh" should read --of a seventh--
Column 13, Line 32: "foe present" should read --the present--
Column 13, Line 35: "mount 46" should read --mount 45--
Column 13, Line 38: "venous fine" should read --venous line--
Column 13, Line 66: "sections 814, 918" should read --sections 914, 916--
Column 14, Line 5: "or the tike" should read --or the like--
Column 14, Line 9: "which wifi" should read --which will--
Column 14, Line 10: "tire application" should read --the application--
Column 14, Line 14: "tire unfurled" should read --the unfurled--
Column 14, Line 32: "surface white" should read --surface while--
Column 14, Line 35: "sheet-tike" should read --sheet-like--
Column 14, Line 55: "deployed stale" should read --deployed state--
Column 14, Line 65: "end is intended to be used as e support" should read --and is intended to be used as a support--
Column 15, Line 4: "with ell previous" should read --with all previous--
Column 15, Line 6: "axis t-L" should read --axis L-L--
Column 15, Line 8: "26c" should read --25c--
Column 15, Line 30: "(issue anchor" should read --tissue anchor--
Column 15, Line 33: "with and relative to" should read --with and displaceable relative to--
Column 15, Line 38: "barbs 1428" should read --barbs 1426--
Column 15, Line 51: "but feeling radially" should read --but facing radially--
Column 15, Line 65: "barbs 1628" should read --barbs 1626--
Column 15, Line 65: "bias m the form" should read --bias in the form--
Column 16, Line 13: "anchor 1810" should read --anchor 1610--
Column 16, Line 14: "first section 1814" should read --first section 1614--
Column 16, Line 16: "second section 1618" should read --second section 1616--
Column 16, Line 17: "anchor 1810" should read --anchor 1610--
Column 16, Line 19: "anchor 1810" should read --anchor 1610--
Column 16, Line 20: "barbs 1628 rotated" should read --barbs 1626 rotated--
Column 16, Line 20: "towards the barbs 162B" should read --towards the barbs 1628--
Column 16, Line 29: "second section 1718" should read --second section 1716--
Column 16, Line 47: "microneedles 1828, 1828" should read --microneedles 1826, 1828--
Column 16, Line 48: "sections 1814, 1618" should read --sections 1814, 1816--
Column 16, Line 56: "FIG. 38c, At feast some" should read --FIG. 38c. At least some--
Column 16, Line 57: "preferably at" should read --preferably all--
Column 16, Line 67: "1828, 1828" should read --1826, 1828--
Column 17, Line 28: "30 printing" should read --3D printing--

CERTIFICATE OF CORRECTION (continued)
U.S. Pat. No. 11,298,124 B2

Column 17, Line 38: "30 rapid-prototyping" should read --3D rapid-prototyping--
Column 17, Line 48: "m total" should read --in total--
Column 18, Line 28: "Embodiments A and 8" should read --Embodiments A and B--
Column 18, Line 39: "1 kN load ceil" should read --1kN load cell--
Column 18, Line 50: "mechanics) anchors" should read --mechanical anchors--
Column 19, Line 15: "buttered formalin" should read --buffered formalin--
Column 19, Line 28: "Imaged (NiH)" should read --ImageJ (NIH)--
Column 19, Line 29: "tee vertical" should read --the vertical--
Column 19, Line 54: "tee skin" should read --the skin--
Column 19, Line 63: "fallowing example" should read --following example--
Column 20, Line 18: "Embodiment 8" should read --Embodiment B--
Column 20, Lines 25-26: "Embodiment 8" should read --Embodiment B--
Column 20, Line 32: "fine extending" should read --line extending--
Column 20, Line 53: "16 minutes" should read --15 minutes--
Column 20, Line 67: "tire devices" should read --the devices--
Column 21, Line 1: "In an cases" should read --In all cases--
Column 21, Line 13: "(EMC)" should read --(EMG)--
Column 21, Line 18: "elect rode" should read --electrode--
Column 21, Line 29: "fight sanding" should read --light sanding--
Column 21, Line 40: "20 90871" should read --20.90871--
Column 21, Line 41: "Embodiment 8" should read --Embodiment B--
Column 21, Line 43: "Embodiment 8" should read --Embodiment B--

In the Claims
Claim 1, Column 21, Line 59: "substantially A perpendicular" should read --substantially perpendicular--
Claim 2, Column 21, Line 65: "first direction" should read --first X direction--
Claim 17, Column 22, Line 48: "second protrusions" should read --second protrusion--
Claim 19, Column 22, Line 66: "second protrusions" should read --second protrusion--
Claim 20, Column 23, Line 5: "second protrusions" should read --second protrusion--